United States Patent
Mandeen et al.

(10) Patent No.: US 9,339,294 B2
(45) Date of Patent: May 17, 2016

(54) INSTRUMENTS FOR CONTROLLED DELIVERY OF INJECTABLE MATERIALS INTO BONE

(71) Applicant: ZIMMER KNEE CREATIONS, INC., Exton, PA (US)

(72) Inventors: Christopher D. Mandeen, West Chester, PA (US); Shaun B. Hanson, West Chester, PA (US); David L. Nichols, West Chester, PA (US)

(73) Assignee: ZIMMER KNEE CREATIONS, INC., Exton, PA (US)

( * ) Notice: Subject to any disclaimer, the term of this patent is extended or adjusted under 35 U.S.C. 154(b) by 248 days.

(21) Appl. No.: 14/021,785

(22) Filed: Sep. 9, 2013

(65) Prior Publication Data
US 2014/0074102 A1    Mar. 13, 2014

Related U.S. Application Data

(60) Provisional application No. 61/697,943, filed on Sep. 7, 2012, provisional application No. 61/784,707, filed on Mar. 14, 2013.

(51) Int. Cl.
| | | |
|---|---|---|
| *A61B 17/58* | (2006.01) | |
| *A61B 17/60* | (2006.01) | |
| *A61F 2/00* | (2006.01) | |
| *A61B 17/34* | (2006.01) | |
| *A61B 17/17* | (2006.01) | |
| *A61B 17/16* | (2006.01) | |
| *A61B 19/00* | (2006.01) | |

(52) U.S. Cl.
CPC ......... *A61B 17/3472* (2013.01); *A61B 17/1604* (2013.01); *A61B 17/1764* (2013.01); *A61B 19/30* (2013.01); *A61B 2019/304* (2013.01); *A61B 2019/306* (2013.01); *A61B 2019/307* (2013.01); *A61B 2019/462* (2013.01)

(58) Field of Classification Search
CPC combination set(s) only.
See application file for complete search history.

(56) References Cited

U.S. PATENT DOCUMENTS

| | | |
|---|---|---|
| 5,514,137 A | 5/1996 | Coutts |
| 5,556,429 A | 9/1996 | Felt |
| 5,755,809 A | 5/1998 | Cohen |
| 6,140,452 A | 10/2000 | Felt |

(Continued)

FOREIGN PATENT DOCUMENTS

| | | |
|---|---|---|
| FR | 2170919 A1 | 9/1973 |
| FR | 2885512 A1 | 11/2006 |

(Continued)

OTHER PUBLICATIONS

"International Application Serial No. PCT/IB2013/002698, International Search Report mailed Jun. 10, 2014", 6 pgs.

(Continued)

*Primary Examiner* — Sameh Boles
(74) *Attorney, Agent, or Firm* — Schwegman Lundberg & Woessner, P.A.

(57) ABSTRACT

Instruments for treating bone defects of the joint, particularly at the subchondral level, such as bone marrow lesions or bone marrow edema, are provided. In particular, these instruments may be delivery instruments that comprise features to control the location to which they deliver injectable materials or other tools to the bone to be treated. Also provided is an injection instrument that delivers a treatment material to the bone defect and stimulates a natural healing response in the bone.

11 Claims, 19 Drawing Sheets

(56) References Cited

U.S. PATENT DOCUMENTS

| | | |
|---|---|---|
| 6,235,043 B1 | 5/2001 | Reiley |
| 6,241,734 B1 | 6/2001 | Scribner |
| 6,248,110 B1 | 6/2001 | Reiley |
| 6,306,177 B1 | 10/2001 | Felt |
| 6,395,007 B1 | 5/2002 | Bhatnager |
| 6,564,083 B2 | 5/2003 | Stevens |
| 6,607,561 B2 | 8/2003 | Brannon |
| 6,613,054 B2 | 9/2003 | Scribner |
| 6,719,761 B1 | 4/2004 | Reiley |
| 6,746,451 B2 | 6/2004 | Middleton |
| 6,827,720 B2 | 12/2004 | Leali |
| 6,863,899 B2 | 3/2005 | Koblish |
| 6,887,246 B2 | 5/2005 | Bhatnager |
| 7,153,307 B2 | 12/2006 | Scribner |
| 7,261,720 B2 | 8/2007 | Stevens |
| 7,708,742 B2 | 5/2010 | Scribner |
| 7,771,431 B2 | 8/2010 | Scribner |
| 7,811,290 B2 | 10/2010 | Rabiner |
| 8,062,364 B1 | 11/2011 | Sharkey et al. |
| 8,152,813 B2 | 4/2012 | Osorio |
| 8,168,692 B2 | 5/2012 | Wenz |
| 2003/0138473 A1 | 7/2003 | Koblish |
| 2005/0119219 A1 | 6/2005 | Bellini |
| 2006/0064164 A1 | 3/2006 | Thelen |
| 2007/0066987 A1 | 3/2007 | Scanlan et al. |
| 2008/0071281 A1* | 3/2008 | Wilson ............... A61F 2/4611 606/92 |
| 2010/0076503 A1 | 3/2010 | Beyar |
| 2010/0179549 A1 | 7/2010 | Keller |
| 2011/0125156 A1 | 5/2011 | Sharkey et al. |
| 2011/0125157 A1 | 5/2011 | Sharkey et al. |
| 2011/0125159 A1 | 5/2011 | Hanson et al. |
| 2011/0125200 A1 | 5/2011 | Hanson et al. |
| 2011/0125201 A1 | 5/2011 | Hanson et al. |
| 2011/0125264 A1 | 5/2011 | Bagga et al. |
| 2011/0125265 A1 | 5/2011 | Bagga et al. |
| 2011/0125272 A1 | 5/2011 | Bagga et al. |
| 2012/0245645 A1 | 9/2012 | Hanson et al. |
| 2012/0316513 A1 | 12/2012 | Sharkey et al. |

FOREIGN PATENT DOCUMENTS

| | | |
|---|---|---|
| WO | WO-9004364 A1 | 5/1990 |
| WO | WO-2009070896 A1 | 6/2009 |
| WO | WO-2014045124 A2 | 3/2014 |
| WO | WO-2014045124 A3 | 3/2014 |

OTHER PUBLICATIONS

"International Application Serial No. PCT/IB2013/002698, Invitation to Pay Additional Fees and Partial Search Report mailed Mar. 27, 2014", 5 pgs.

"International Application Serial No. PCT/IB2013/002698, Written Opinion mailed Jun. 10, 2014", 8 pgs.

"International Application Serial No. PCT/IB2013/002698, International Preliminary Report on Patentability mailed Mar. 19, 2015", 10 pgs.

* cited by examiner

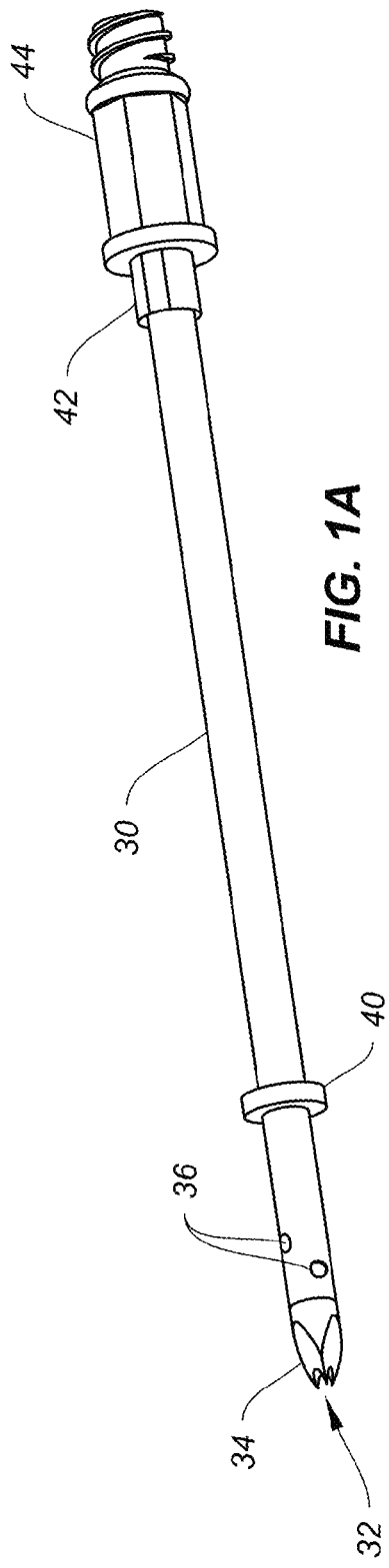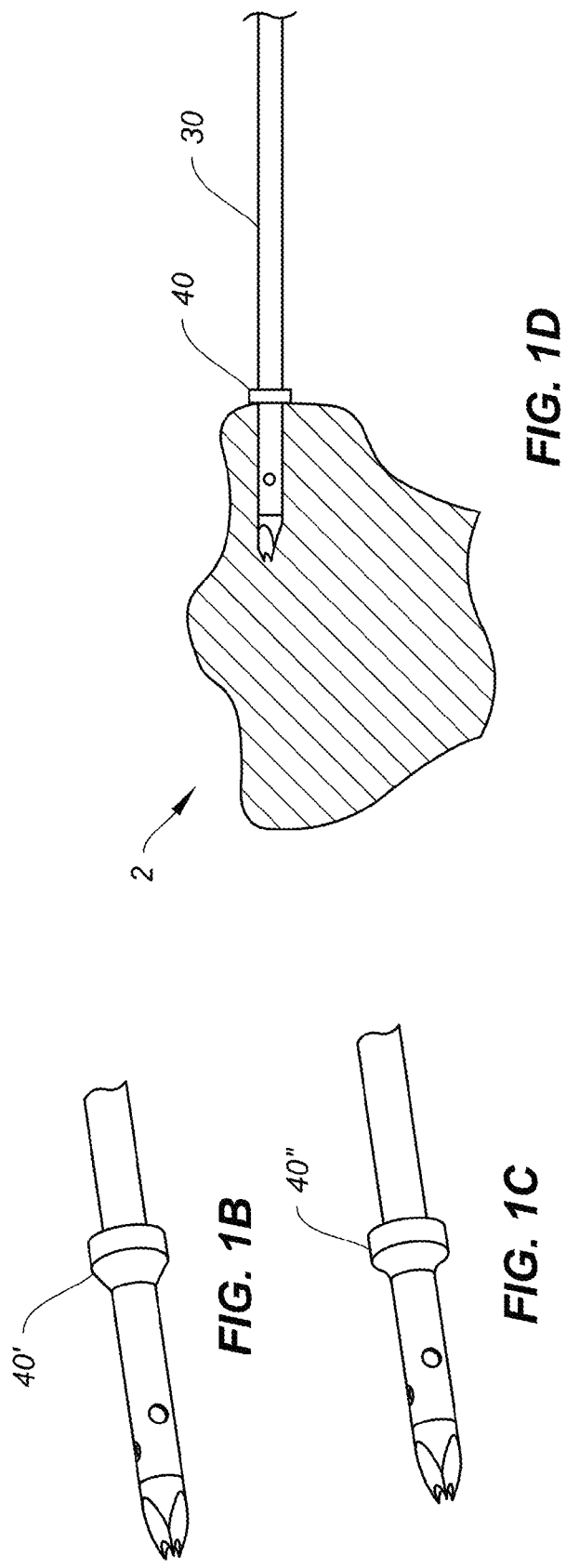

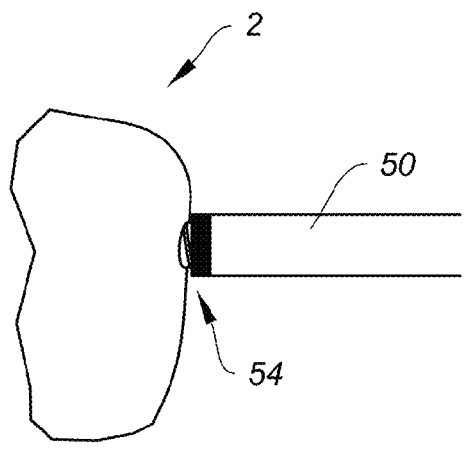
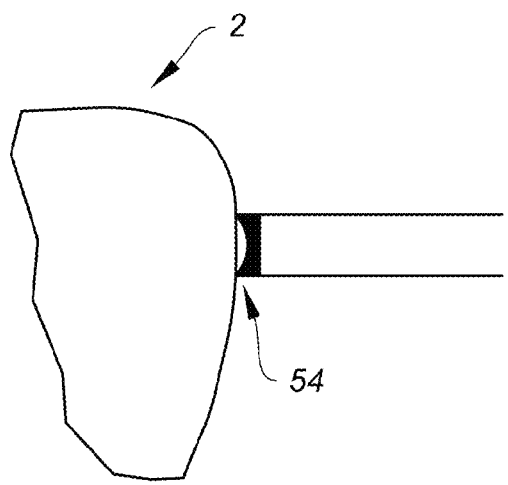
FIG. 4A  FIG. 4B
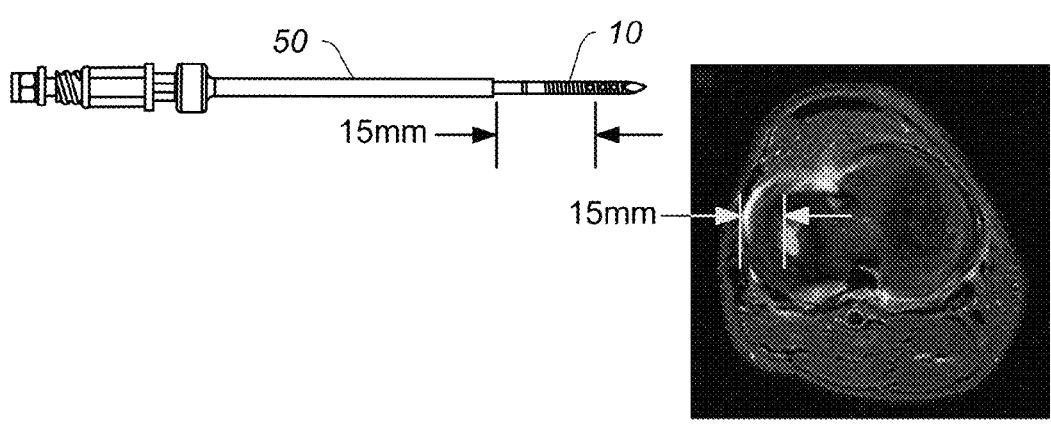
FIG. 5

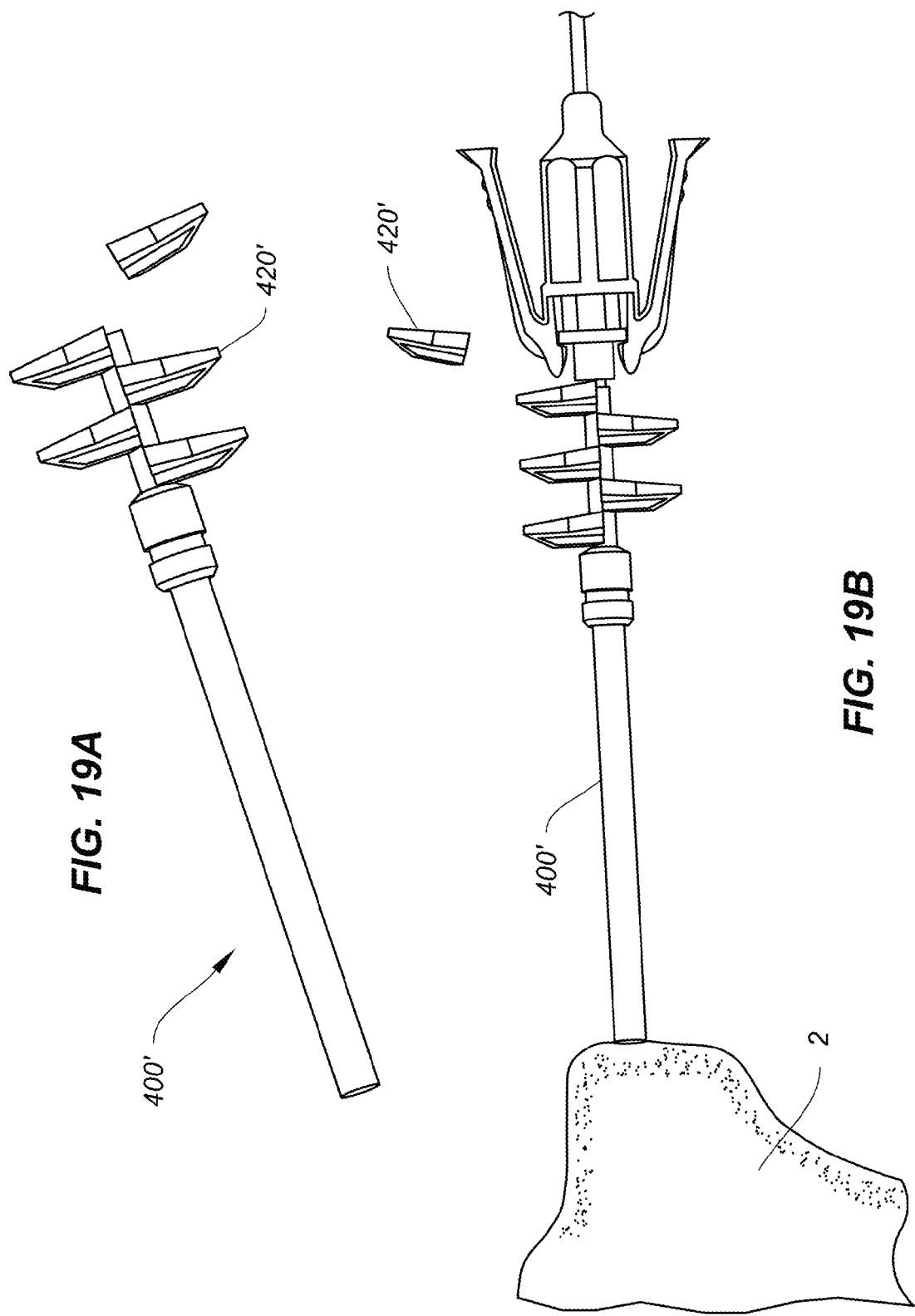

INSTRUMENTS FOR CONTROLLED DELIVERY OF INJECTABLE MATERIALS INTO BONE

CROSS-REFERENCE TO RELATED APPLICATIONS

This application claims priority to U.S. Provisional No. 61/697,943 filed Sep. 7, 2012 and U.S. Provisional No. 61/784,707 filed Mar. 14, 2013, both of which are entitled "INSTRUMENTS FOR CONTROLLED DELIVERY OF INJECTABLE MATERIALS INTO BONE," the contents of which are incorporated by reference in their entirety.

FIELD

The present invention relates to medical instruments for the surgical treatment of subchondral bone defects, especially at or near a joint, and associated methods. Even more particularly, the medical instruments provide controlled delivery of injectable materials into bone for treatment of the subchondral bone defect.

BACKGROUND

Human joints, in particular the knee, hip and spine, are susceptible to degeneration from disease, trauma, and long-term repetitive use that eventually lead to pain. Knee pain, for example, is the impetus for a wide majority of medical treatments and associated medical costs. The most popular theory arising from the medical community is that knee pain results from bone-on-bone contact or inadequate cartilage cushioning. These conditions are believed to frequently result from the progression of osteoarthritis, which is measured in terms of narrowing of the joint space. Therefore, the severity of osteoarthritis is believed to be an indicator or precursor to joint pain. Most surgeons and medical practitioners thus base their treatments for pain relief on this theory. For example, the typical treatment is to administer pain medication, or more drastically, to perform some type of joint resurfacing or joint replacement surgery.

However, the severity of osteoarthritis, especially in joints such as the knee and ankle, has been found to correlate poorly with the incidence and magnitude of knee pain. Because of this, surgeons and medical practitioners have struggled to deliver consistent, reliable pain relief to patients especially if preservation of the joint is desired.

Whether by external physical force, disease, or the natural aging process, structural damage to bone can cause injury, trauma, degeneration or erosion of otherwise healthy tissue. The resultant damage can be characterized as a bone defect that can take the form of a fissure, fracture, microfracture, lesion, edema, tumor, or sclerotic hardening, for example. Particularly in joints, the damage may not be limited to a bone defect, and may also include cartilage loss (especially articular cartilage), tendon damage, and inflammation in the surrounding area.

Patients most often seek treatment because of pain and deterioration of quality of life attributed to the osteoarthritis. The goal of surgical and non-surgical treatments for osteoarthritis is to reduce or eliminate pain and restore joint function. Both non-surgical and surgical treatments are currently available for joint repair.

Non-surgical treatments include weight loss (for the overweight patient), activity modification (low impact exercise), quadriceps strengthening, patellar taping, analgesic and anti-inflammatory medications, and with corticosteroid and/or viscosupplements. Typically, non-surgical treatments, usually involving pharmacological intervention such as the administration of non-steroidal anti-inflammatory drugs or injection of hyaluronic acid-based products, are initially administered to patients experiencing relatively less severe pain or joint complications. However, when non-surgical treatments prove ineffective, or for patients with severe pain or bone injury, surgical intervention is often necessary.

Surgical options include arthroscopic partial meniscectomy and loose body removal. Most surgical treatments conventionally employ mechanical fixation devices such as screws, plates, staples, rods, sutures, and the like are commonly used to repair damaged bone. These fixation devices can be implanted at, or around, the damaged region to stabilize or immobilize the weakened area, in order to promote healing and provide support. Injectable or fillable hardening materials such as bone cements, bone void fillers, or bone substitute materials are also commonly used to stabilize bone defects.

High tibial osteotomy (HTO) or total knee arthroplasty (TKA) is often recommended for patients with severe pain associated with osteoarthritis, especially when other non-invasive options have failed. Both procedures have been shown to be effective in treating knee pain associated with osteoarthritis.

However, patients only elect HTO or TKA with reluctance. Both HTO and TKA are major surgical interventions and may be associated with severe complications. HTO is a painful procedure that may require a long recovery. TKA patients often also report the replaced knee lacks a "natural feel" and have functional limitations. Moreover, both HTO and TKA have limited durability. Accordingly, it would be desirable to provide a medical procedure that addresses the pain associated with osteoarthritis and provides an alternative to a HTO or TKA procedure.

Many of these medical procedures require internal access into the bone to be treated. It is known to access the subchondral level of bone using a tool such as a pin, wire, needle, cannula, etc. to access and treat a subchondral bone defect. Accordingly, it would be desirable to provide instruments that control the location to which these tools are drilled or forced into the bone.

SUMMARY

The present disclosure provides instruments for treating bone defects of the joint, particularly at the subchondral level, such as bone marrow lesions or bone marrow edema. In particular, these instruments may be tool delivery instruments that comprise features to control the location to which they deliver the tool to the bone to be treated.

In one exemplary embodiment, a pin for delivering treatment material to a subchondral bone defect is provided. The pin may comprise a cannulated shaft extending between a tip and a tool-engaging end, the shaft including one or more fenestrations near the tip, and a depth control collar around the shaft.

In another exemplary embodiment, a delivery instrument for delivering treatment material to a subchondral bone defect is provided. The delivery instrument may comprise a pin comprising a cannulated shaft extending between a tip and a tool-engaging end. The shaft may include one or more fenestrations near the tip. For example, in one embodiment, the tip may comprise cutting edges. A depth control sleeve configured to slide over the pin may be provided. The sleeve may comprise a depth control collar that abuts a portion of the pin to prevent overdrilling of the pin into bone.

In yet another embodiment, a guide for drilling into a subchondral level of bone is provided. The guide may comprise one or more drilling portals, one or more trajectory indicators, and an attachment mechanism for repeated and accurate attachment to a patient's leg. The trajectory indicators may be viewed under fluoroscopy.

In still another exemplary embodiment, an injection instrument for delivering treatment material to a subchondral bone defect of a joint is provided. The instrument may comprise a cannulated instrument having a bent neck extending into an open port. The open port may be surrounded by surface enhancement features sufficient to puncture through cartilage and bone. The instrument may further including a tool-engaging end for attachment to an injection system, and an inner stylus formed of a conformable material for insertion and removal in and out of the cannulated instrument.

In yet another embodiment, a removable spacer clip for depth control is provided. The spacer clip may comprise a C-shaped body with extendable arms and a seat in between for receiving a tubular body such as a delivery pin or cannula. The spacer clip may be configured for placement over a tubular body to control depth of insertion of the tubular body relative to a stationary object.

In still an even further embodiment, an adjustable spacer body for depth control is provided. The spacer body may comprise a tubular body for receiving a tubular drilling instrument. The tubular body may include a plurality of space segments, each spacer segment representing a predetermined length of the tubular body. The spacer segment may be attached to the tubular body at a structurally weakened area to enable breakaway removal of the spacer segment in increments.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

FIG. 1A shows an exemplary embodiment of a cannulated delivery pin of the present disclosure having a depth insertion control feature.

FIGS. 1B and 1C show enlarged views of alternative depth control features on the cannulated delivery pin of FIG. 1A.

FIG. 1D shows the cannulated delivery pin of FIG. 1A in use in situ.

FIGS. 4A and 4B show enlarged views of other exemplary embodiments of a delivery instrument in situ.

FIG. 5 compares relative dimensions of the delivery instrument of FIG. 2B with a bone marrow edema as seen on an MRI.

FIG. 19A shows still another exemplary embodiment of an adjustable spacer body of the present disclosure.

FIG. 19B shows the adjustable spacer body of FIG. 19A in situ.

DESCRIPTION OF THE EMBODIMENTS

Figure 2A:
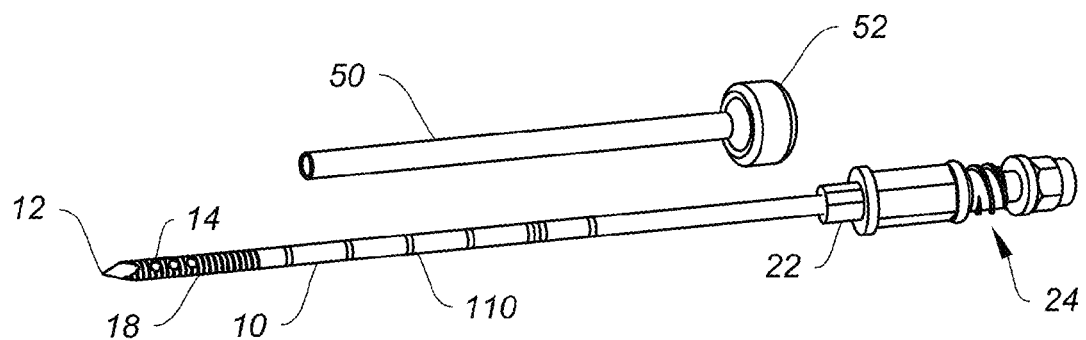
FIG. 2A shows an exploded view of an exemplary embodiment of a delivery instrument comprising a pin and depth control sleeve combination.

Methods, devices and instruments for treating joint pain to restore natural joint function and preserving, as much as possible, the joint's articular and cartilage surface are known. Treatments through the joint that violate the articular and cartilage surface often weaken the bone and have unpredictable results. Rather than focusing on treatment of pain through the joint, alternative treatments that diagnose and treat pain at its source in the subchondral region of a bone of a joint to relieve the pain are provided. Pain associated with joints, especially osteoarthritic joints, can be correlated to bone defects or changes at the subchondral level rather than, for example, the severity of osteoarthritic progression or defects at the articular surface level. In particular, bone defects, such as bone marrow lesions, edema, fissures, fractures, hardened bone, etc. near the joint surface lead to a mechanical disadvantage and abnormal stress distribution in the periarticular bone, which may cause inflammation and generate pain. By altering the makeup of the periarticular bone (which may or may not be sclerotic) in relation to the surrounding region, it is possible to change the structural integrity of the affected bone and restore normal healing function, thus leading to a resolution of the inflammation surrounding the defect.

Treatment of the bone by mechanical and biological means to restore the normal physiologic stress distribution, and restore the healing balance of the bone tissue at the subchondral level, is a more effect way of treating pain than conventional techniques. That is, treatment can be effectively achieved by mechanically strengthening or stabilizing the defect, and biologically initiating or stimulating a healing response to the defect. Methods, devices, and systems for a subchondral procedure that achieve these goals are disclosed in co-owned U.S. Pat. No. 8,062,364 entitled "OSTEOARTHRITIS TREATMENT AND DEVICE" as well as in co-owned and co-pending U.S. Patent Application Publication Nos. 2011/0125156 entitled "METHOD FOR TREATING JOINT PAIN AND ASSOCIATED INSTRUMENTS" and 2011/0125157 entitled "SUBCHONDRAL TREATMENT OF JOINT PAIN," both of which were filed on Nov. 19, 2010, the contents of which are incorporated by reference in their entirety. This subchondral procedure, and its associated devices, instruments, etc. are also marketed under the registered trademark name of SUBCHONDROPLASTY™. The SUBCHONDROPLASTY™ procedure is a response to a desire for an alternative to patients facing partial or total knee replacement.

In general, the SUBCHONDROPLASTY™ or SCP™ technique is intended to both strengthen the bone and stimulate the bone. In an SCP™ procedure, bone fractures or nonunions are stabilized, integrated or healed, which results in reduction of a bone defect, such as a bone marrow lesion or edema. In addition, the SCP™ procedure restores or alters the distribution of forces in a joint to thereby relieve pain. The SCP™ procedure can be performed arthroscopically or percutaneously to treat pain by stabilizing chronic stress fracture, resolving any chronic bone marrow lesion or edema, and preserving, as much as possible, the articular surfaces of the joint. The SUBCHONDROPLASTY™ procedure generally comprises evaluating a joint, for example, by taking an image of the joint, detecting the presence of one or more subchondral defects, diagnosing, which of these subchondral defects is the source of pain, and determining an extent of treatment for the subchondral defect. The technique is particularly suited for treating chronic defects or injuries, where the patient's natural healing response has not resolved the defect. It should be noted, however, that the technique is equally applicable to treatment of defects in the subchondral region of bone where the defect is due to an acute injury or from other violations. Several exemplary treatment modalities for the SCP™ procedure for the different extents of treatment needed can be employed. Accordingly, a medical practitioner may elect to use the techniques and devices described herein to subchondrally treat any number of bone defects, as he deems appropriate.

Detection and identification of the relevant bone marrow lesion or bone marrow edema (BML or BME) can be achieved by imaging, e.g., magnetic resonance imaging (MRI), X-ray, bone scans, manual palpation, chemical or biological assay, and the like. A T1-weighted MRI can be used to detect sclerotic bone, for example. Another example is that a T2-weighted MRI can be used to detect lesions, edemas, and cysts. X-ray imaging may be suitable for early-stage as well as end-stage arthritis. From the imaging, certain defects may be identified as the source of pain. In general, defects that are associated with chronic injury and chronic deficit of healing are differentiated from defects that result, e.g., from diminished bone density. SCP™ treatments are appropriate for a BML or BME that may be characterized as a bone defect that is chronically unable to heal (or remodel) itself, which may cause a non-union of the bone, stress or insufficiency fractures, and perceptible pain. Factors considered may include, among other things, the nature of the defect, size of the defect, location of the defect, etc. For example, bone defects at the edge near the articular surface of periphery of a joint may be often considered eligible for treatment due to edge-loading effects as well as the likelihood of bone hardening at these locations. A bone defect caused by an acute injury would generally be able to heal itself through the patient's own natural healing process. However, in such situations where the bone defect is due to an acute injury and either the defect does not heal on its own, or the medical practitioner decides that the present technique is appropriate, SCP™ treatment can be administered on acute stress fractures, BML or BME, or other subchondral defects, as previously mentioned.

The SCP™ treatment may continue after surgery. In particular, the patient may be monitored for a change in pain scores, or positive change in function. For example, patients are also checked to see when they are able to perform full weight-bearing activity and when they can return to normal activity. Of note, the SCP™ procedure can be revised and thus allows for optional further treatment in the event that a patient requires or desires a joint replacement or other type of procedure. The procedure does not exclude a future joint repair or replacement treatment to be applied, and thus may also be performed in conjunction with other procedures, such as cartilage resurfacing, regeneration or replacement, if desired. In those instances where additional treatment is desired, the SCP™ treated area may remain undisturbed while the additional treatment is performed, such as where cartilage resurfacing is desired. Alternatively, the SCP™ treated area can be removed, and not create an obstacle to the additional treatment, such as where a partial or total joint replacement is desired. Advantageously, the SCP™ treatment may be provided as a first or initial treatment, reserving for the future and possibly forestalling until a later date than otherwise might be the case more invasive treatments such as partial or total joint replacement.

Various surgical treatments to address subchondral defects known as bone marrow lesions have previously been attempted. Between May and November 2008, three (3) surgeries were performed at Riddle Hospital in Media, Pennsylvania in the United States. On May 12, 2008, Dr. Peter F. Sharkey performed a right knee arthroscopy with arthroscopically assisted stabilization of a patient's right knee with a medial tibial plateau fracture. During the procedure, a cannulated bone biopsy needle was placed into the bone under fluoroscopic guidance, and augmentation material was injected. The injected augmentation material was Stryker Orthopedics Hydroset (Bone Substitute Material). The surgeon expressed difficulty in injecting the bone substitute material.

On Oct. 27, 2008, Dr. Steven B. Cohen performed a left knee arthroscopy, partial medial meniscectomy, drilling of osteochondral lesion using retrograde technique, and debridement chondroplasty of patellofemoral chondrosis on a patient's left knee with medial meniscus tear and left knee osteochondral defect with bone marrow lesion of the medial femoral condyle. During the procedure, an Anterior Cruciate Ligament (ACL) portal-creation device was repurposed for this surgery. The tibial probe was placed on the medial femoral condyle, with the tunnel guide secured proximally on the thigh. The surgeon expressed difficulty in positioning and stabilizing the guide. A cannulated pin was placed through the tunnel guide and placed distally into the medial femoral condyle. No implantable material was injected into the bone in this case.

On Nov. 10, 2008, Dr. Steven B. Cohen performed a right knee arthroscopic-assisted repair of a tibial plateau fracture bone marrow lesion with subchondral fracture using bone cement, partial medial and partial lateral meniscectomy to treat medial meniscus tear, and arthroscopic debridement and chondroplasty of medial, lateral, and patellofemoral compartments to treat compartment chondrosis. During the procedure, a guide pin was inserted into the medial tibial plateau, and an endo button drill bit was used to expand the drill hole. One (1) cubic centimeter (cc) of cement was inserted into the bone. A second drill hole was made from below, and a second cubic centimeter (cc) of cement was inserted into the bone.

The experiences gained from these previous surgeries helped to develop the fundamental theories underlying the SUBCHONDROPLASTY™ procedure and the number of treatment modalities, associated devices, instruments and related methods of use for performing the SUBCHONDROPLASTY™ procedure, which are disclosed in the aforementioned publications. These treatment modalities may be used alone or in combination, as will be described in detail below.

In one treatment modality, the subchondral bone in the region of the bone marrow lesion or defect can be strengthened by introduction of a hardening material, such as a bone substitute, at the site. The bone substitute may be an injectable calcium phosphate ensconced in an optimized carrier material. In an SCP™ procedure, the injected material may also serve as a bone stimulator that reinvigorates the desired acute bone healing activity.

For example, polymethylmethacrylate (PMMA) or calcium phosphate (CaP) cement injections can be made at the defect site. PMMA injection may increase the mechanical strength of the bone, allowing it to withstand greater mechanical stresses. CaP cement injection may also increase the mechanical strength of the bone, while also stimulating the localized region for bone fracture repair. In one embodiment, the injection can be made parallel to the joint surface. In another embodiment, the injection can be made at an angle to the joint surface. In yet another embodiment, the injection can be made below a bone marrow lesion. Preferably, the injection is made without disrupting the joint surface.

In another treatment modality, the subchondral bone region can be stimulated to trigger or improve the body's natural healing process. For example, in one embodiment of this treatment modality, one or more small holes may be drilled at the region of the defect to increase stimulation (e.g., blood flow, cellular turnover, etc.) and initiate a healing response leading to bone repair. In another embodiment, after holes are drilled an osteogenic, osteoinductive, or osteoconductive agent may be introduced to the site. Bone graft material, for example, may be used to fill the hole. This treatment modality may create a better load-supporting environment leading to long term healing. Electrical or heat stimulation may also be employed to stimulate the healing process of a chronically injured bone. Chemical, biochemical and/or biological stimulation may also be employed in an SCP™ procedure. For instance, stimulation of bone tissue in an SCP™ procedure may be enhanced via the use of cytokines and other cell signaling agents to trigger osteogenesis, chondrogenesis, and/or angiogenesis to perhaps reverse progression of osteoarthritis.

In yet another treatment modality, an implantable device may be implanted into the subchondral bone to provide mechanical support to the damaged or affected bone region, such as where an insufficiency fracture or stress fracture has occurred. The implant may help create a better load distribution in the subchondral region. In the knees, the implant may support tibio-femoral compressive loads. In addition, the implant may mechanically integrate sclerotic bone with the surrounding healthy bone tissue. The implants may be place in cancellous bone, through sclerotic bone, or under sclerotic bone at the affected bone region. The implant may also be configured as a bi-cortical bone implant. In one embodiment, one side of the implant can be anchored to the peripheral cortex to create a cantilever beam support (i.e., a portion of the implant is inserted into bone but the second end stays outside or near the outer surface of the bone). The implant may be inserted using a guide wire. In one example, the implant may be inserted over a guide wire. In another example, the implant may be delivered through a guide instrument.

The implant may further be augmented with a PMMA or CaP cement injection, other biologic agent, or an osteoconductive, osteoinductive and/or osteogenic agent. The augmentation material may be introduced through the implant, around the implant, and/or apart from the implant but at the affected bone region, such as into the lower region of a bone marrow lesion or below the lesion. For example, the implant may act as a portal to inject the augmentation material into the subchondral bone region.

While each of the above-mentioned treatment modalities may be administered independent of one another, it is contemplated that any combination of these modalities may be applied together and in any order so desired, depending on the severity or stage of development of the bone defect(s). Suitable implantable fixation devices for the surgical treatment of these altered bone regions or bone defects, especially at the subchondral level, are disclosed in co-pending and co-owned U.S. Patent Application Publication No. 2011/0125265 entitled "IMPLANTABLE DEVICES FOR SUBCHONDRAL TREATMENT OF JOINT PAIN," U.S. Patent Application Publication No. 2011/0125264 entitled "IMPLANTABLE DEVICES FOR SUBCHONDRAL TREATMENT OF JOINT PAIN," and U.S. Patent Application Publication No. 2011/0125272 entitled "BONE-DERIVED IMPLANTABLE DEVICES FOR SUBCHONDRAL TREATMENT OF JOINT PAIN," all of which were filed on Nov. 19, 2010, the contents of which are herein incorporated in their entirety by reference. These devices and instruments can be use in combination with cements or hardening materials commonly used to repair damaged bone by their introduction into or near the site of damage, either to create a binding agent, cellular scaffold or mechanical scaffold for immobilization, regeneration or remodeling of the bone tissue. As previously stated, treatment of the bone defect at the subchondral level preferably is performed without disrupting the joint surface.

In a healthy joint such as a tibio-femoral joint, the compressive load between the contact bones (i.e., the femur and the tibia) is properly distributed, thus keeping the contact stresses in the cartilage to a reasonably low level. As the cartilage starts to wear out or degenerate locally, the tibio-femoral contact area reduces and starts to get localized at the site of the cartilage defect. The localization of the stresses may also occur due to varus or valgus deformity. Sometimes, the condition may occur because of osteoporosis, where bone becomes weak and is no longer able to support normal loads. This condition leads to higher localized contact stresses in the cartilage, and the subchondral region below the cartilage. Once the stresses reach beyond a certain threshold level, it leads to defects like bone marrow lesions and edema, and perhaps generates knee pain. If the problem persists, the high contact stresses can lead to sclerotic bone formation as well. The presence of sclerotic bone can compromise vascularization of the local area, and also create a mechanical mismatch in the bone tissue. This mismatch may start to expedite degeneration of all parts of the joint leading to increased levels of osteoarthritis.

Pain associated with osteoarthritic joints can be correlated to bone defects or changes at the subchondral level. In particular, bone defects such as bone marrow lesions, edema, fissures, fractures, etc. near the joint surface lead to abnormal stress distribution in the periarticular bone, which may or may not cause inflammation and generate pain. By altering the makeup of the periarticular bone (which may or may not be sclerotic) in relation to the surrounding region, it is possible to change the structural integrity of the affected bone, leading to a resolution of the inflammation. Treatment of the bone in an effort to alter the structural makeup of the affected periarticular bone leads to reduced inflammation and pain has proven to be successful. Over time, restoration of normal physiologic stress distribution can be achieved in load bearing joints such as the hip and knee, and mechanical congruity restored, thereby resulting in healing of the inflammation and reduction or elimination of pain.

In general, the present disclosure provides embodiments related to instruments and associated methods for the surgical treatment of a joint, and particularly a bone defect at that joint region. More specifically, the embodiments relate to instruments for treating a bone defect of a joint at the subchondral level and associated methods. These instruments and devices may be used in a manner consistent with the subchondral procedures previously described, and may contain depth control features for more accuracy.

As previously mentioned, instruments and tools to carry out the SCP™ techniques mentioned above, such as pins, needles, cannulas, wires, etc. have been disclosed for treatment of subchondral defects in bone joints. The delivery pins of the present disclosure may be similar to those disclosed in co-pending and co-owned U.S. Patent Application Publication No. 2012/0316513, filed Jun. 8, 2012 and entitled "INSTRUMENTS AND DEVICES FOR SUBCHONDRAL JOINT REPAIR," the contents of which are incorporated by reference in their entirety. The instruments and tools of the present disclosure, however, also include depth control features to provide the user with greater accuracy and control over their insertion. Turning now to the drawings, FIG. 1A shows an exemplary embodiment of a cannulated delivery pin 30 of the present disclosure. The pin 30 may be fully cannulated and/or have fenestrations 36, as shown. Also as shown, the pin 30 may have a cannulated opening 32 that may be sharp with teeth, ridges, or cutting edges 34. This pin 10 may be used to deliver an injectable treatment material such as those previously described above in association with SCP™ treatment modalities.

Surrounding the shaft of the cannulated delivery pin 30 may be a collar 40. This collar 40 may be located at a specified distance from the tip of the pin 30. The collar may act as a hard stop, as shown in FIG. 1D where the pin 30 is used in bone 2 in situ, or may be tapered to make insertion into bone progressively harder. FIGS. 1B and 1C show alternative embodiments in which the collar 40', 40" may be differently curved or tapered to achieve a different effect as it is inserted into bone 2. Accordingly, as the pin 30 is drilled into bone 2, the collar 40 buttresses up against the cortical bone. At that point, the pin 30 would stop advancing, or the process of inserting becomes noticeably more difficult (i.e., greater force is required to advance the pin 30).

The cannulated delivery pin 30 may also include a shoulder portion 42 and an adapter or tool-engaging end 44 to connect to other components, such as for example, an injection system or syringe, to deliver materials through the pin 30.

FIG. 2A shows an exploded view of an exemplary embodiment of a delivery instrument comprising a delivery pin 10 and depth control sleeve 50. The pin 10 may be of a fenestrated and/or cannulated variety, similar to those previously described by applicants, and can include a sharpened insertion tip 12, fenestrations 14, and threads or other surface features 18. The sleeve 50 may be cannulated to fit over the pin 10, and may optionally include a depth control collar 52 at the end, as shown in FIGS. 2A and 2B.

Figure 2B:
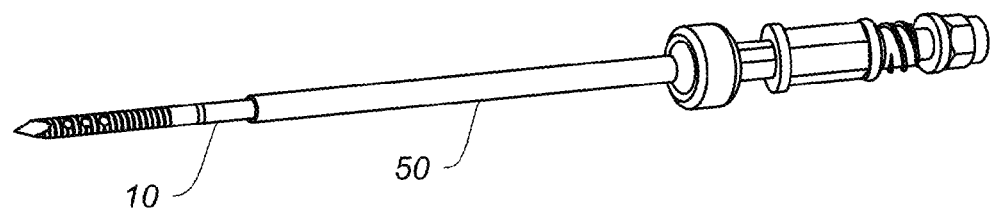
FIG. 2B shows the assembled delivery instrument of FIG. 2A.

FIG. 2B shows the assembled instrument with the depth control sleeve 50 slid over the pin 10. As shown, in use, the collar 52 of the sleeve 50 buttresses against the shoulder 22 near the adapter or tool-engaging end 24 of the pin 10, while the tip of the sleeve 50 would rest against cortical bone. The sleeve 50 therefore acts as a wedge between the cortical bone and the pin 10, and serves to prevent the pin 10 from being drilled deeper than desired into the bone.

Figure 3A:
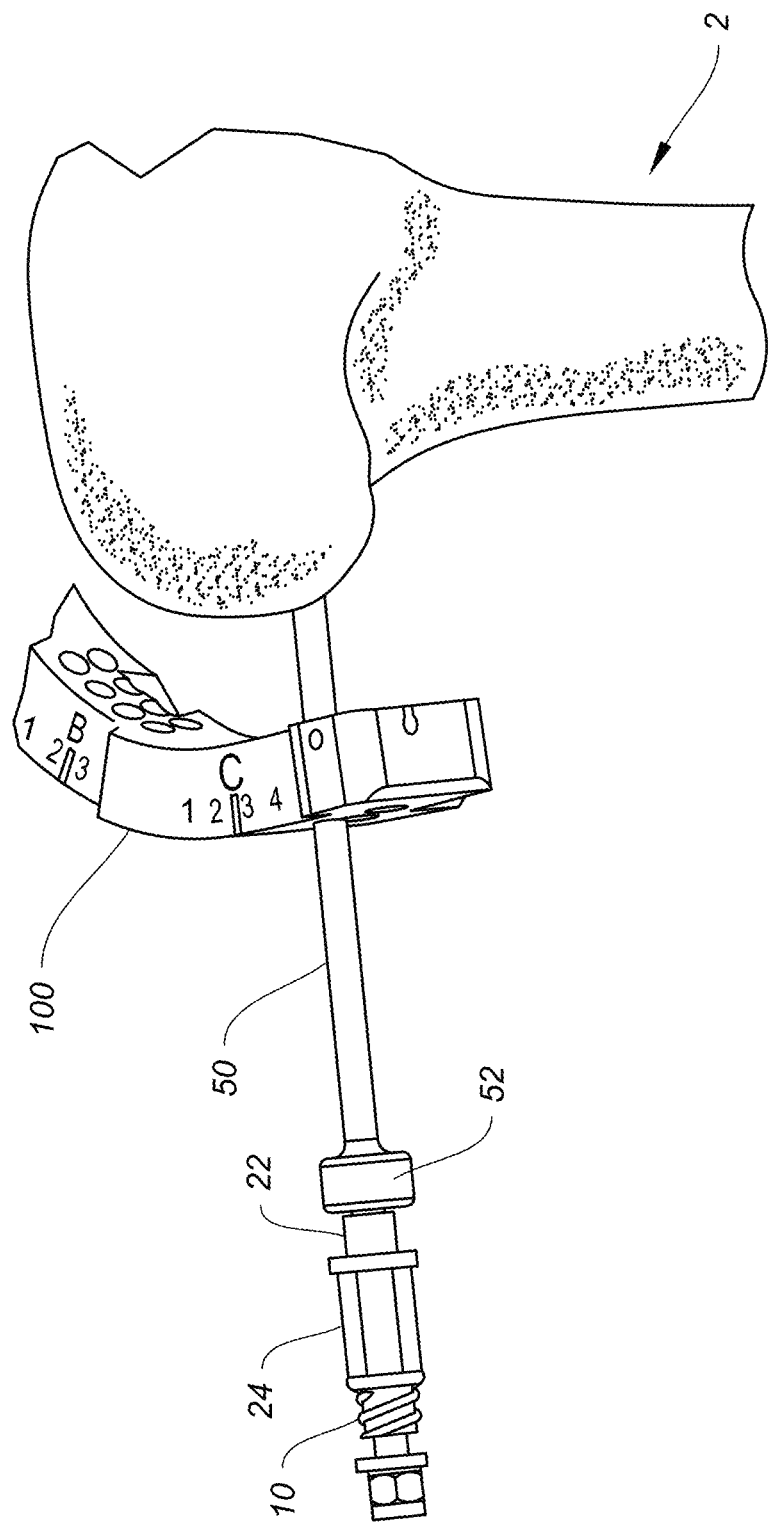
FIGS. 3A-3D illustrate an exemplary method of using the assembled delivery instrument of FIG. 2B in use with an exemplary navigation guide.
Figure 3B:
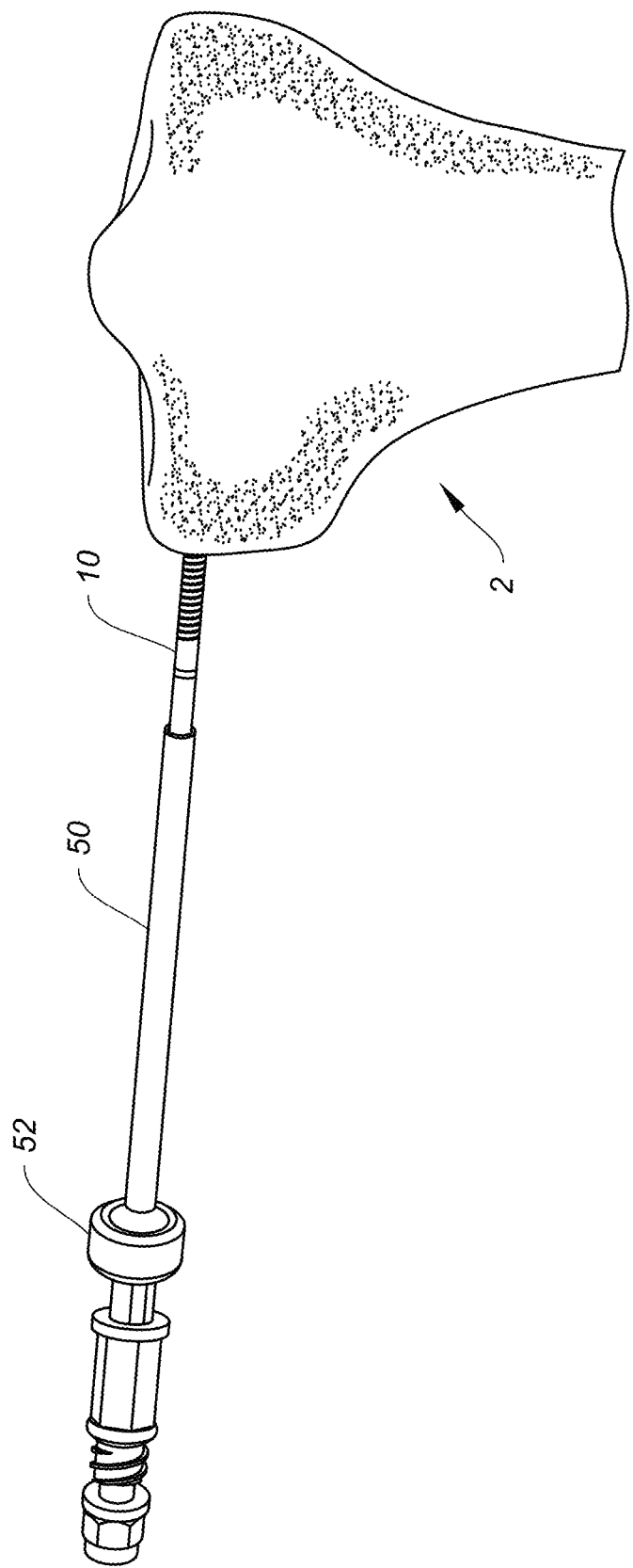

FIGS. 3A-3D illustrate a method of using the assembled delivery instrument of FIG. 2B with a navigation or template guide similar to those previously described by applicants for navigating to a subchondral region of bone for carrying out SCP™ techniques. In FIG. 3A, the delivery instrument (comprising the pin 10 residing within the sleeve 50) is inserted through a guide 100 to target a location in a subchondral region of bone 2. As shown, the sleeve 50 rests inside the guide 100, up against cortical bone 2, and up against an aspect of the pin 10. The pin 10 cannot be drilled any deeper into the bone 2 because the tip or front end of the sleeve 50 is too thick to puncture the bone 2. It is understood, of course, that the sleeve 50 may or may not be used in conjunction with a guide 100 shown. Further, the portion of the pin 10 that extends beyond (i.e., is longer than) the sleeve 50 is now the portion inside the bone 2.

As previously mentioned, a navigation guide, template guide, or other imaging tool may be provided with the systems of the present disclosure to guide the instrument or device toward the subchondral defect. Such navigation or imaging tools or guides may be used to ascertain a desired access path for targeting the location of the subchondral region near the subchondral defect to be treated. In one example, this access path may be determined using a mapping system that provides a set of coordinates for targeting the location of the subchondral region. Such a mapping system may be similar to the one disclosed in co-pending and co-owned U.S. Patent Application Publication No. 2011/0125201, filed Nov. 19, 2010 and entitled "COORDINATE MAPPING SYSTEM FOR JOINT TREATMENT," the contents of which are herein incorporated in their entirety by reference.

In addition to the mapping system described above, other navigation or imaging tools suitable for use with the systems and methods of the present disclosure may include those disclosed in co-pending and co-owned U.S. Patent Application Publication No. 2011/0125159, filed Nov. 19, 2010 and entitled "INSTRUMENTS FOR A VARIABLE ANGLE APPROACH TO A JOINT," U.S. Patent Application Publication No. 2011/0125200, filed Nov. 19, 2010 and entitled "NAVIGATION AND POSITIONING INSTRUMENTS FOR JOINT REPAIR AND METHODS OF USE," U.S. Patent Application Publication No. 2012/0245645, filed Feb. 22, 2012 and entitled "NAVIGATION AND POSITIONING SYSTEMS AND GUIDE INSTRUMENTS FOR JOINT REPAIR," and U.S. patent application Ser. No. 14/022,001, also published as U.S. Patent Applicatioin Publication No. 2014/0074117 filed on Sep. 9, 2013 and entitled "NAVIGATION INSTRUMENTS FOR SUBCHONDRAL BONE TREATMENT," the contents of which are herein incorporated in their entirety by reference.

It is contemplated that these depth control components such as the depth control sleeve 50 may serve multiple functions. For example, the depth control components allow the user to confirm that the pin 10 has sufficiently penetrated the cortical shell such that the cannulation and/or fenestrations are inside the bone 2 to be treated. In addition, the components minimize or stop extravasation of injectable materials of the type disclosed above and associated with SCP™ techniques, like bone substitute material, from the access area into the bone 2. Also, the components ensure that the port of the injection pin 10 reaches the prescribed proximity for the bone defect, such as the bone marrow edema or lesion. The components also serve as a stop to prevent over-advancement of the pin 10. This would include stopping it from progressing past the bone marrow edema or lesion, or through the bone 2, as an added safety feature. Accordingly, the sleeve acts to prevent extravasation by covering up the fenestrations that are either not in use, or are exposed as the pin 50 is removed from the area.

Figure 3C:
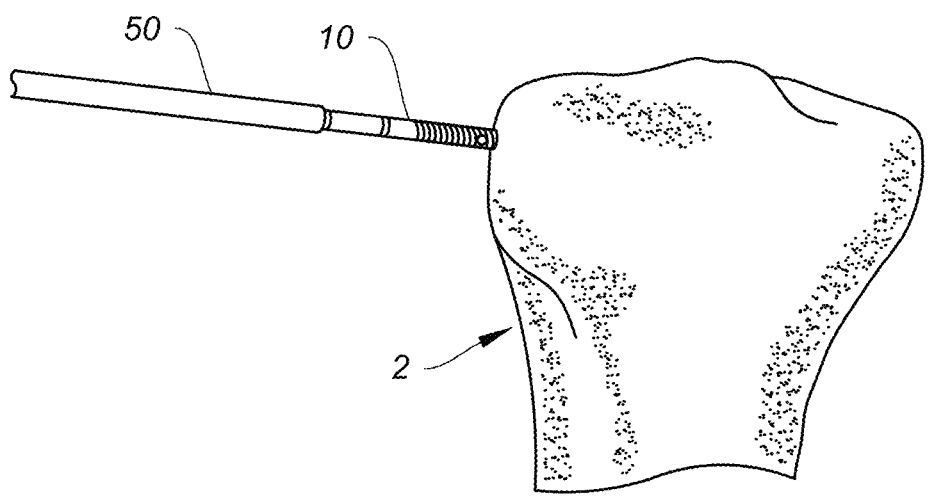
Figure 3D:
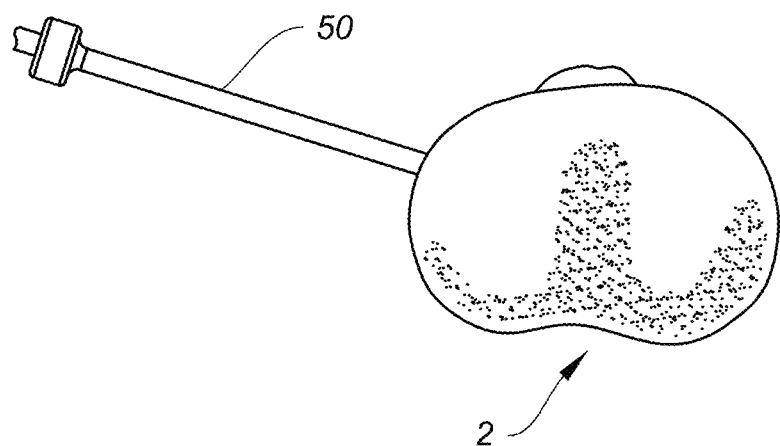

The ability to provide sufficient penetration of a pin 10 to the bone defect provides a significant advantage. 2D imaging (C-arm, e.g.) has been known to give misleading depth representations depending on the viewing angle. For example, in FIG. 3B the fenestrations of the pin 10 appear to be fully inserted. In FIG. 3C, which is a rotated view of FIG. 3B, it can be seen that the last fenestration is still proud. A depth sleeve 50 or collar would serve as a tactile confirmation that the tip of the pin 10 has been inserted sufficiently to cover the fenestrations, regardless of the viewing angle, as shown in FIG. 3D.

In another exemplary embodiment of the sleeve 50 of the present disclosure, the depth control sleeve 50 may have a conformable end 54, as shown in situ in FIGS. 4A and 4B. This conformable end 54 may be formed of a conformable material, such as rubber or silicone, and would contour to the bone 2 as the sleeve 50 is pressed up to it, thereby creating a type of seal. This feature would minimize the potential for extravasation as the pressure builds up inside the bone 2 from the insertion/injection. In another embodiment, the end of the sleeve 50 may be formed of metal, and drilled into the bone 2 slightly to create a tight seal with the bone 2, achieving the same sealing effect as mentioned. The conformable end 54 may be flat, as shown in FIG. 4A, or may be curved, as shown in FIG. 4B.

It is contemplated that these sleeves 50 may also be used to insert one or more fenestration or port to a prescribed depth to reach the bone defect. FIG. 5 compares relative dimensions of the delivery instrument of FIG. 2A with a bone marrow edema as seen on an MRI. As can be seen from the MRI, the defect in this case is an edema 15 mm from the peripheral of the bone 2. The edge of the depth sleeve 50 or collar to the fenestrations of the pin 10 is set to match that depth of 15 mm, as also shown. In some cases, the fenestration could also be cannulation or a combination of the two. When the pin 10 is drilled into the bone 2, the fenestrations or ports will be located at the prescribed edema depth.

Figure 6:
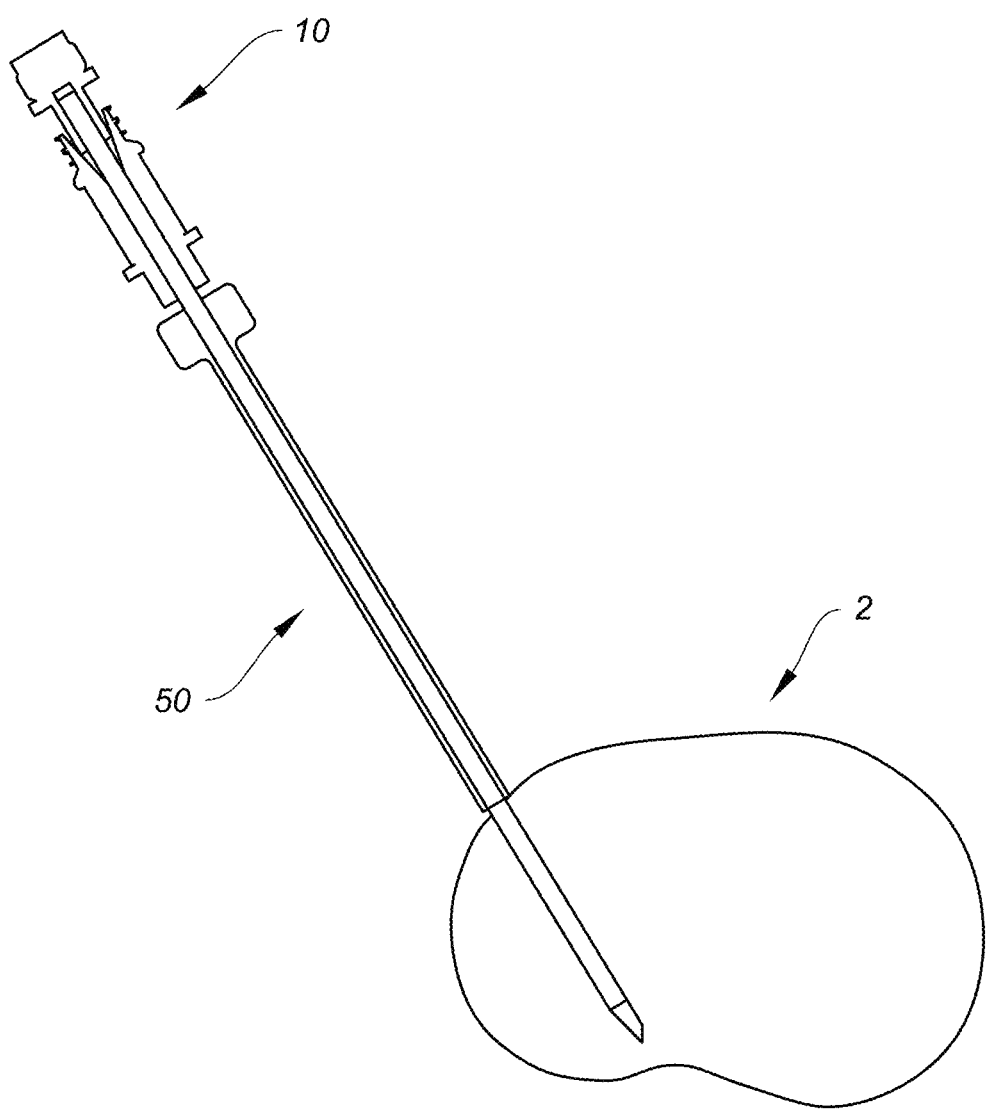
FIG. 6 shows a partial cutaway view of the delivery instrument of FIG. 2B in use.

As mentioned, the depth sleeve 50 can also serve as a safety device to ensure that the pin 10 is not over drilled into, or through, the bone 2. As shown in FIG. 6 the pin 10 inside the depth sleeve 50 is limited in how deep it can enter the bone 2. Any further advancement of that pin 10 and the pin 10 would go through the bone 2; this could result in an ineffective injection of treatment material and could also lead to injury depending on what is in front of the pin's path. However, as shown, the sleeve 50 stops the pin 10 from being plunged any further.

Another role the depth sleeve 50 along with the pin 10 can serve is as a pin cover to block or close off unused fenestrations 36 in order to adjust the level, or amount, of fenestrations 36 exposed for delivery of the injectable material. For example, in a case where the user wants to inject a material near the periphery of the bone 2 to be treated, and only a few fenestrations 36 of many fenestrations 36 along the length of the pin 10 are inside the bone area, the depth sleeve 50 may slid down to the bone surface, and used to cover up any exposed fenestrations 36 that are proud (i.e., lie outside the bone) to prevent unwanted ejection of the material during the procedure.

Figure 7:
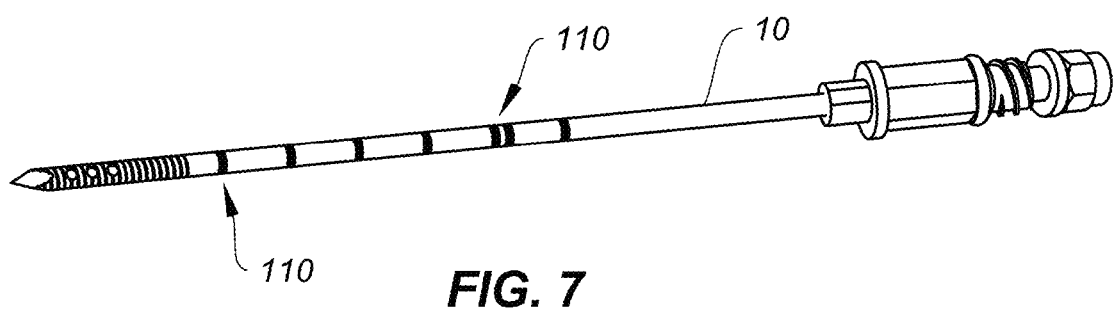
FIG. 7 shows another exemplary embodiment of a cannulated delivery pin of the present disclosure.

As shown in FIG. 7, in another exemplary embodiment of a cannulated delivery pin 10 of the present disclosure, the pin 10 may comprise visual markers 110. These visual markers 110 may contrast to the color of the pin 10, for example. As the pin 10 is drilled into the bone 2, the surgeon can compare the location of these visual markers 110 to a guide so as to ascertain the general distance of advancement.

Figure 8A:
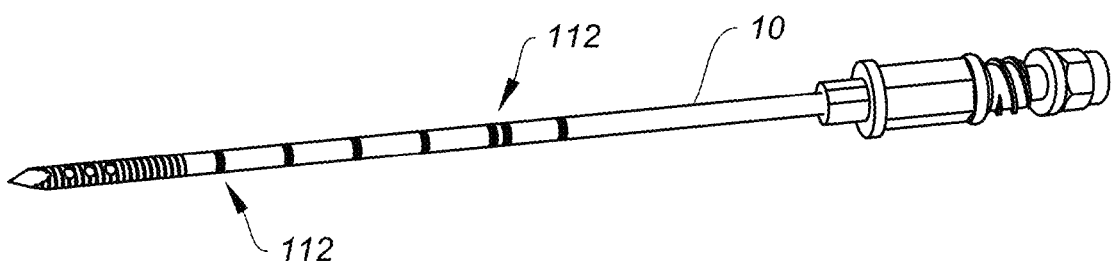
FIGS. 8A and 8B show still another exemplary embodiment of a cannulated delivery pin of the present disclosure.
Figure 8B:
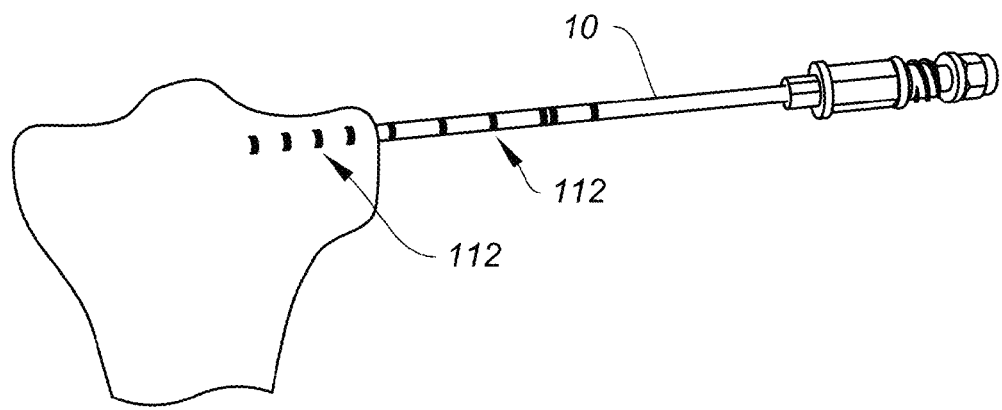

In still another exemplary embodiment of a cannulated delivery pin 10 of the present disclosure, the pin 10 may comprise fluoroscopic or radiopaque/radiolucent markers 112, as shown in FIG. 8A. These fluoroscopic markers 112 would contrast to the material of the pin 10. As the pin 10 is drilled in, surgeons can compare the location of those markers 112 to the contour of the bone 2 under C-arm, as illustrated in FIG. 8B. These markers 112 could be a painted band, metal inlays, or anything else that can be distinguished from the rest of the bone 2 and pin 10.

Figure 9:
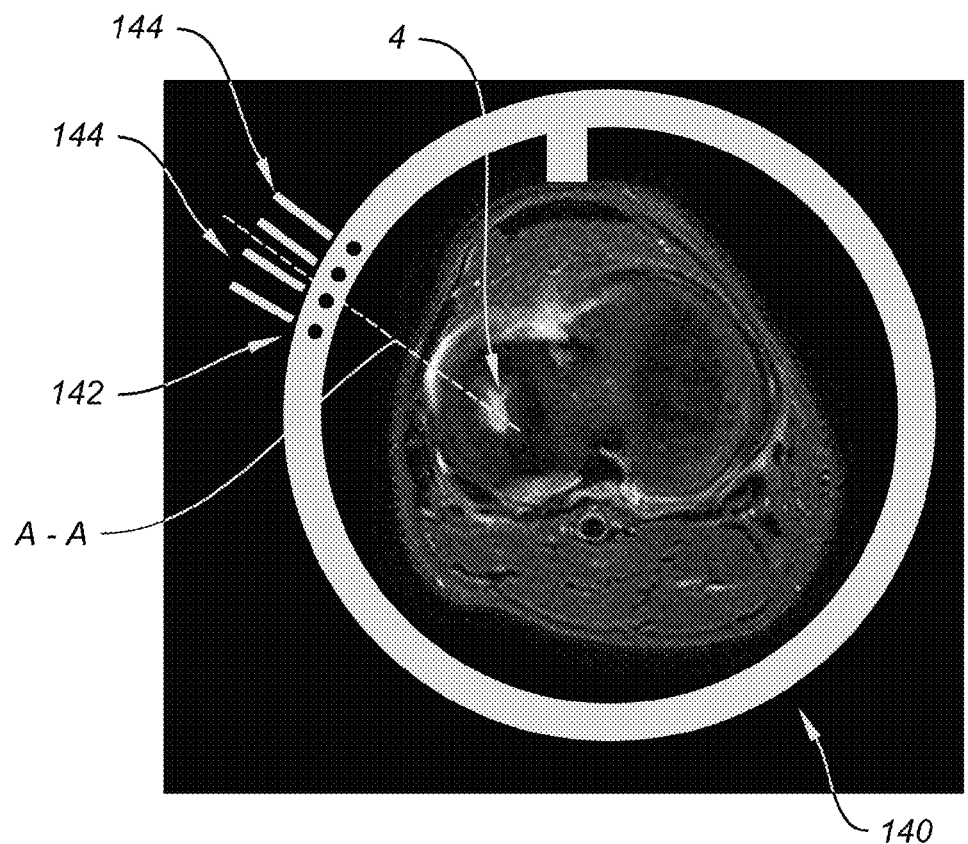
FIG. 9 shows an exemplary embodiment of a guide of the present disclosure in use.

FIG. 9 shows an exemplary embodiment of a guide 140 of the present disclosure used on a bone 2. This guide 140 would be able to be secured and repeatedly attached to the leg of the patient in the same location relative to the bone 2 to be treated. The guide 140 may remain attached to the leg between the steps of taking the MRI and the actual surgery. The guide may have one or more portals 142 for targeting the bone defect 4 (i.e., bone marrow edema or lesion). Trajectory indicators 144 may be part of the guide, thought it is understood that the indicators could be applied to the MRI image after it is taken via a template, tool, or computer program, for example.

This MRI guide 140 may comprise a means to attach to a patient's leg repeatedly, with easy repeatability and accuracy (e.g., screwing into bone, contour to bone/leg, or wrapped to leg). The portals 142 may be configured to facilitate drilling into the body in a controlled direction. The indicators 144 may be configured so that the surgeon can relate the drilling trajectory to the edema 4 on the MRI. Landmarks on the guide 140 may be provided for a template to be placed on the MRI image and a portal 142 selected. The trajectory indicators 144 on the guide 140 can be used by the surgeon to estimate the trajectory and choose an appropriate portal 142, and determine an appropriate access path to the defect, such as line A-A shown. In some situations, the portal 142 may be movable with respect to the attachment area, but in a calculated manner, such that it could be translated back to a template for drilling to the MRI indicated edema 4.

Figure 10:
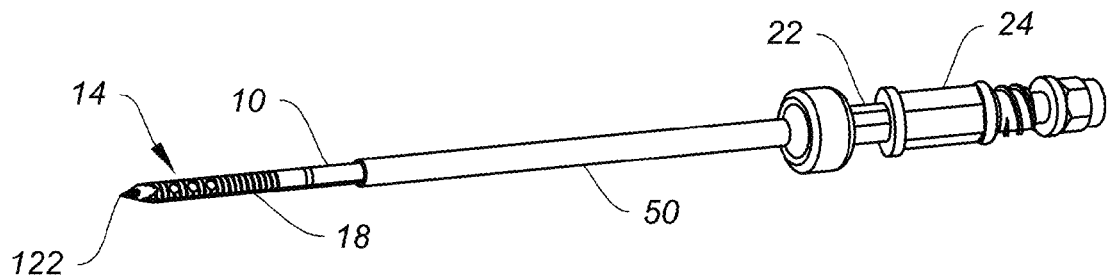
FIG. 10 shows still another exemplary embodiment of a cannulated delivery pin of the present disclosure.

FIG. 10 shows still another exemplary embodiment of a cannulated delivery pin 10 of the present disclosure. In an effort to more accurately indicate that a drilling tip on the pin 10 has reached its intended location, the tip may be configured as a sensory tip 122 to give feedback to the user based on the bone it contacts. The sensory tip 122 may be designed to notice a change in density, temperature, conductivity, inductance, strength, or hardness. It may also indicate when one of these has reached a prescribed threshold. The feedback may be provided as a visual cue (e.g., blinking light, colored LED, etc.) or as an audible cue (e.g., beeping sound). This feature would indicate a proximity or penetration to an edema or lesion to the surgeon so that he may more accurately treat the patient.

Figure 11A:
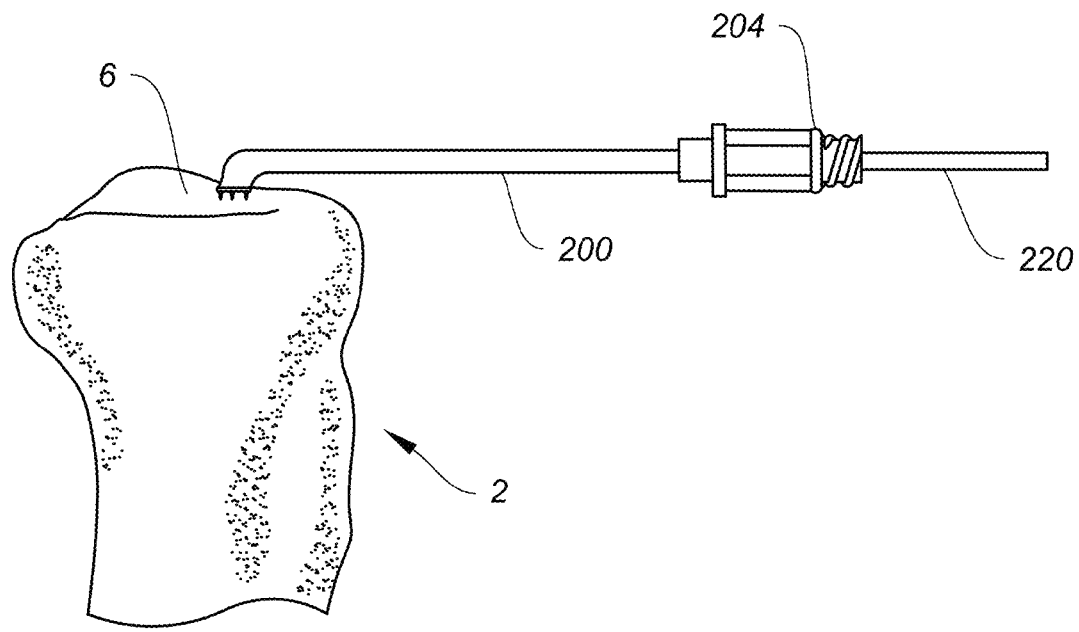
FIGS. 11A-11D illustrate a method of using an exemplary embodiment of an injection instrument in situ.

FIGS. 11A-11D illustrate a method of using an exemplary embodiment of an injection instrument 200 on bone 2. The injection instrument 200 of the present disclosure allows treatment of the bone defect at the subchondral level by breaching the cortical bone in the joint (i.e., articular surface of bone joint) to inject a treatment material to the area to be treated, while simultaneously puncturing the bone 2 to stimulate blood flow and healing. FIG. 11A shows the injection instrument 200 in use on a bone 2. In the present example, the injection instrument 200 is positioned to rest on the tibial surface 6 of the bone 2, ready to be forced into the bone 2 and puncture the surface. The injectable treatment material may be of the kind previously described above in association with SCP™ treatment modalities.

Figure 11B:
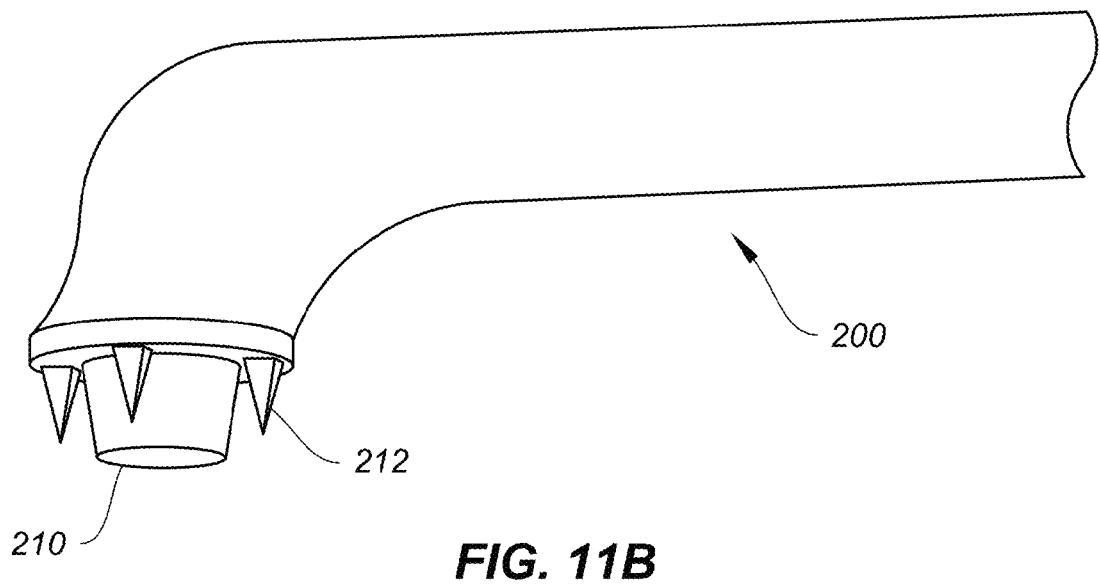
Figure 11C:
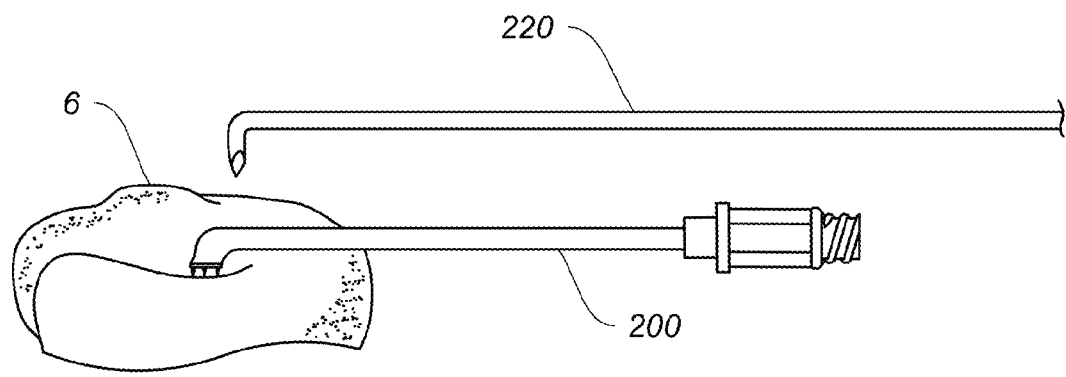
Figure 11D:
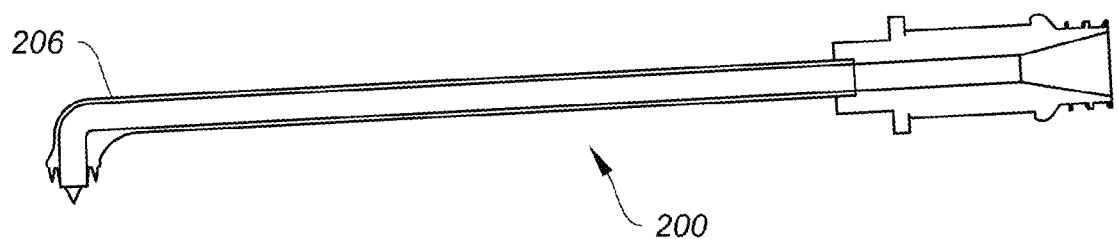

As shown in greater detail in FIGS. 11B-11D, the injection instrument 200 may comprise a back end with adapter system for injection through the instrument 200, such as a Luer Lock 204. A stylus 220 may be inserted into and through the injection instrument 200, as shown in FIG. 11D. Thus, the instrument 200 is fully cannulated after the inner stylus 220 is removed from within, allowing it to be used as an injection port. The injection instrument 200 may comprise a bent neck 206 that extends into an open port 210 surrounding which are surface attachment features like spikes 212, as shown in FIG. 11B. These spikes 212 are configured to puncture cartilage, which punctures would then stimulate blood flow and initial a healing response in the bone after the instrument 200 is removed.

FIG. 11C shows an exploded view of the inner stylus 220 and instrument 200 prior to use on the bone 2. In use, the tip of the stylus may be forced through the instrument 200 and into the cortical bone through the tibial surface 6 of the bone 2. The inner stylus 220 may be formed of a flexible material such as Nitinol, for example, that would enable it to conform and travel in and out of the bent neck 206 of the instrument 200. Once removed from the instrument 200, the injection instrument may be connected to an injection system, such as a syringe filled with a treatment material like bone substitute material. The material can then be injected into the bone, through the tibial surface 6, and into the subchondral level around the defect. The instrument 200 may be manually forced into bone, or a lever-type mechanism may be used to apply force, as will be described in greater detail below.

Figure 12A:
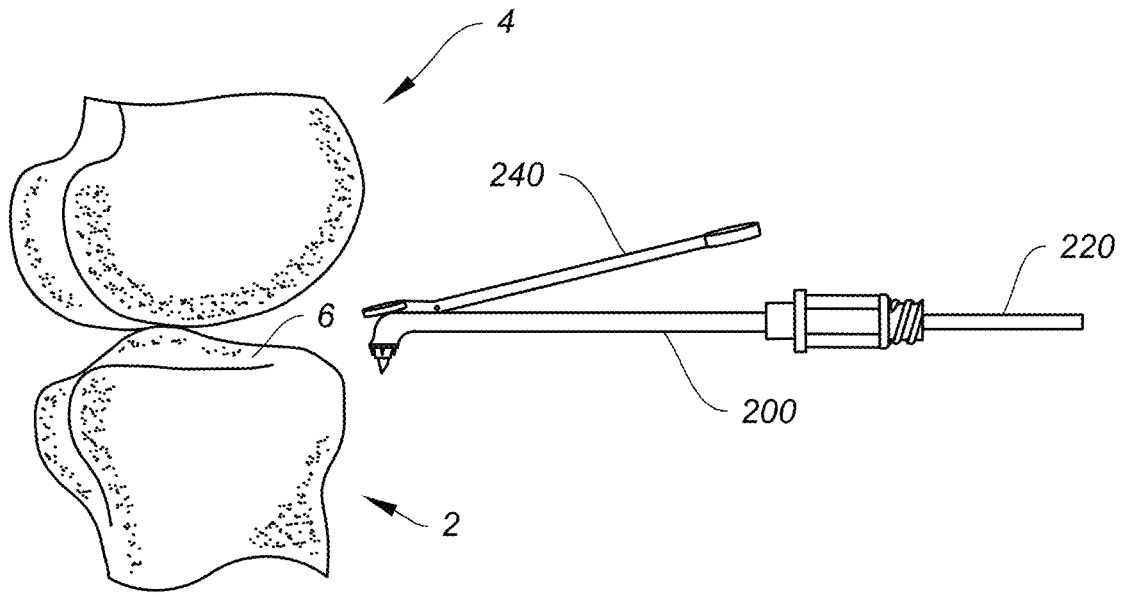
FIGS. 12A-12D illustrate a method of using another exemplary embodiment of an injection instrument on bone.
Figure 12B:
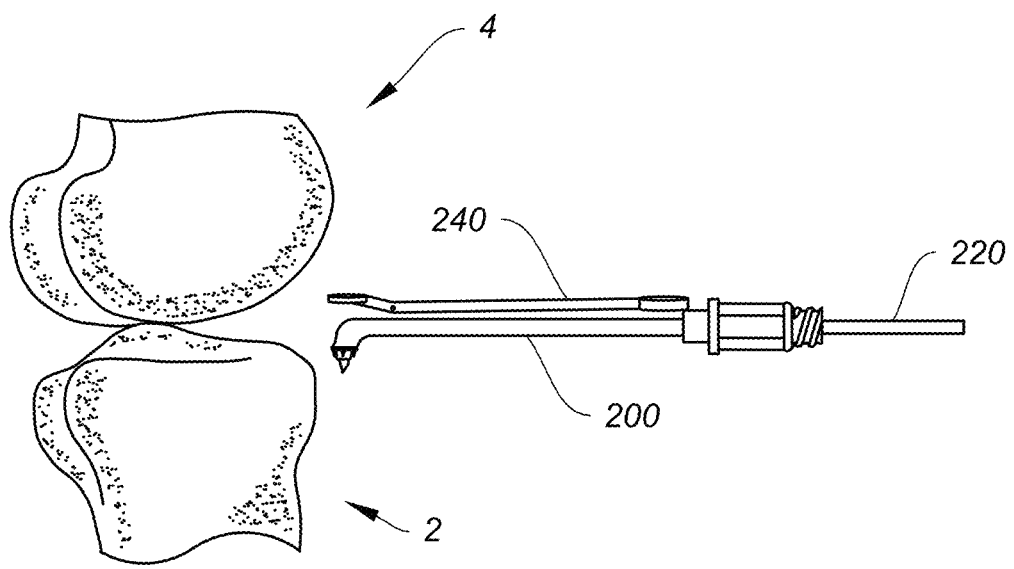
Figure 12C:
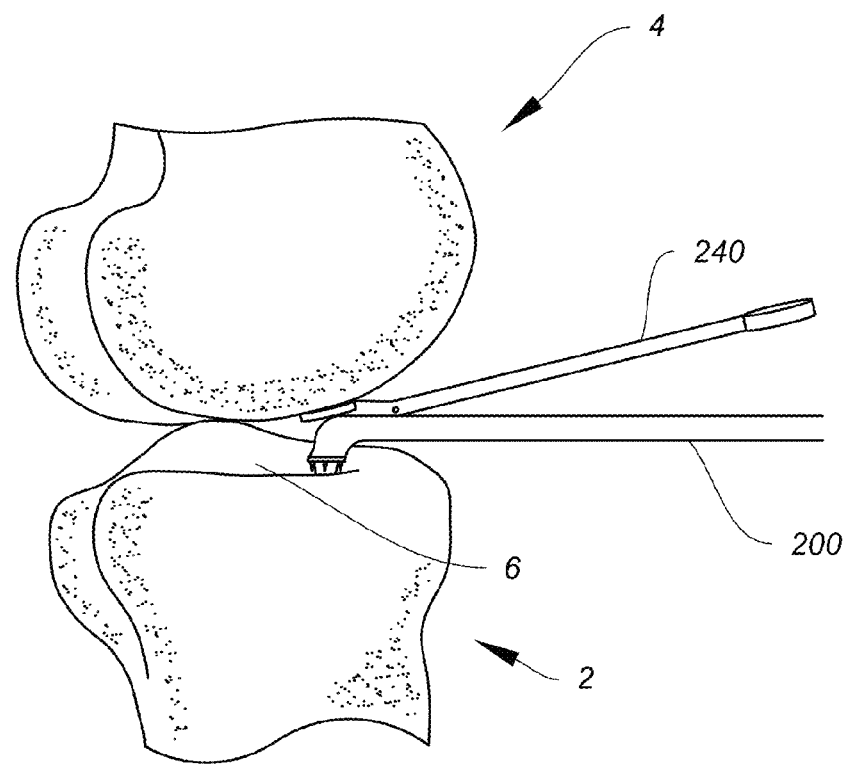
Figure 12D:
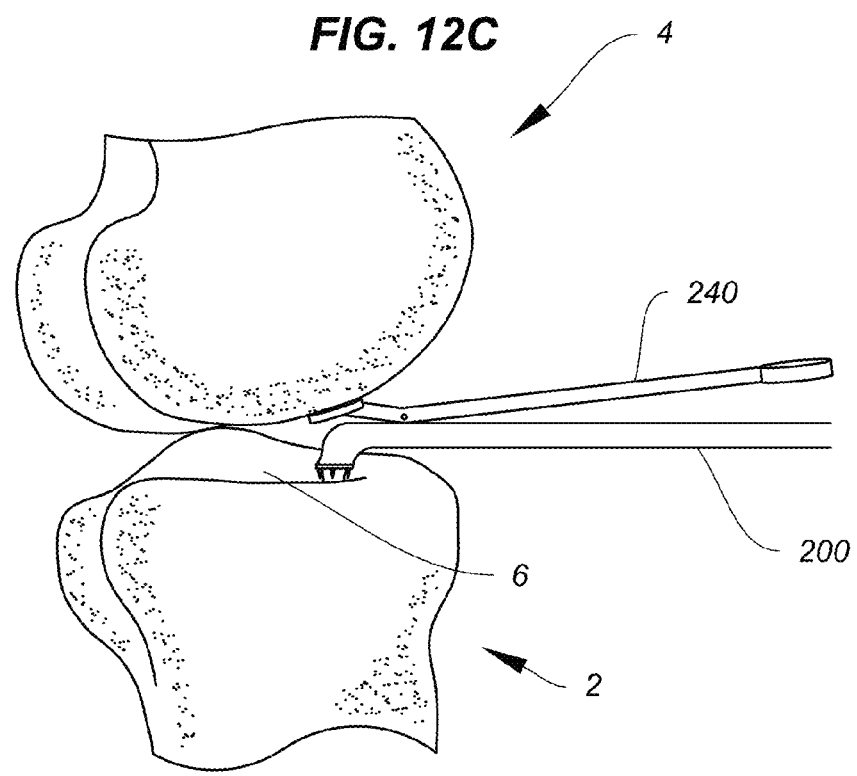

FIGS. 12A-12D illustrate another exemplary embodiment of an injection instrument 200 having an optional lever 240 for greater control. In order to assist the surgeon in forcing the instrument 200 into the cartilage and into the bone, a lever 240 may be provided as shown. This lever 240 helps press the instrument 200 into the bone. As shown in FIG. 12C, in the disengaged position, the instrument 200 does not puncture the joint. Once the lever is engaged or actuated, as shown in FIG. 12D, the tip of the instrument 200 is punctured into the bone.

Although the illustrations and descriptions herein are specific to a knee joint, it is understood that the injection instrument 200 described herein could be used on any joint. The injection instrument provides the benefit of simultaneously creating a port into bone while also puncturing peripheral bone to initiate a healing response. This is achieved when the punctures are vacated (i.e., the instrument 200 is removed) and blood fills the vacancy, thereby triggering the patient's natural healing cascade.

Figure 13:
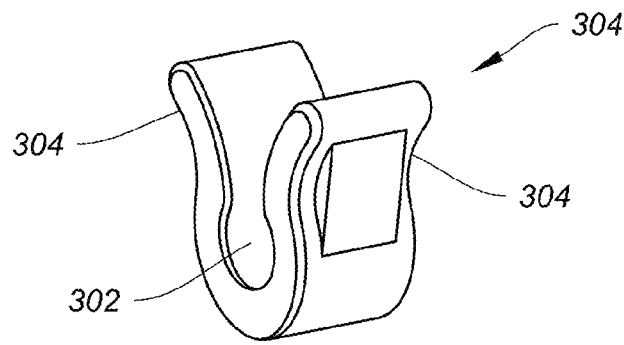
FIG. 13 shows an exemplary embodiment of a removable snap-on spacer of the present disclosure.
Figure 14A:
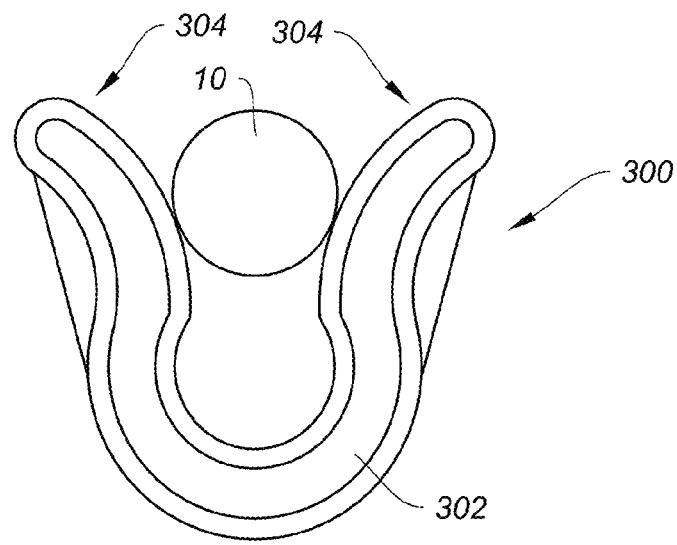
FIGS. 14A and 14B illustrate a method of attaching the snap-on spacer of FIG. 13.
Figure 14B:
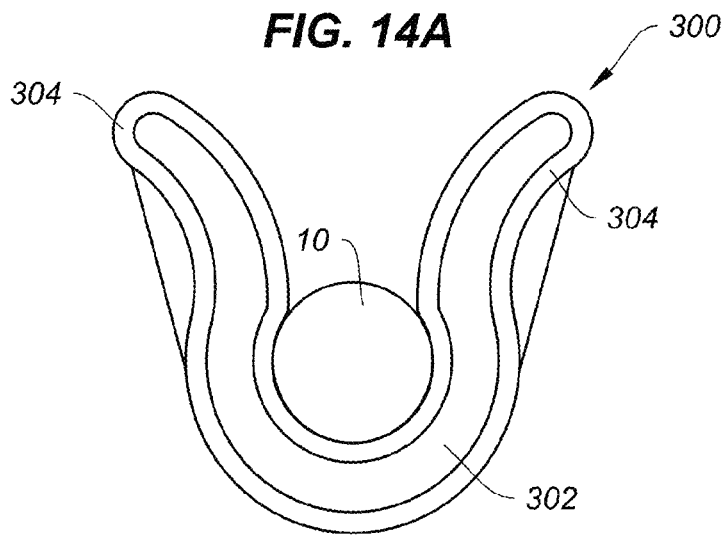

FIG. 13 shows an exemplary embodiment of a spacer 300 that may be easily fitted onto the instruments disclosed herein. The spacer 300 may be configured as a snap-on clip with an open C-shaped body having extendable arms 304. As shown in FIGS. 14A and 14B, the spacer 300 may be expanded to allow the opening to be wide enough to accept the pin 10 or other instrument. In other words, the pin 10 of the delivery instrument may be forced into the C-shaped body 302 with very little effort, and vice versa. The spacer 300 may be easily forced onto the pin 10. The extendable arms 304 enable the clip or spacer 300 to open up enough to receive the pin 10 while also keeping the spacer 300 attached after force is removed.

Figure 15A:
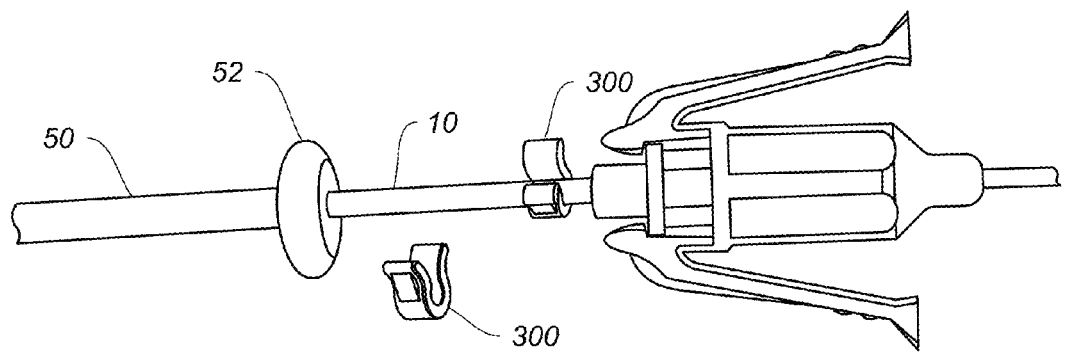
FIG. 15A shows an exploded view of the snap-on spacers of FIG. 13 in use with an exemplary delivery instrument.
Figure 15B:
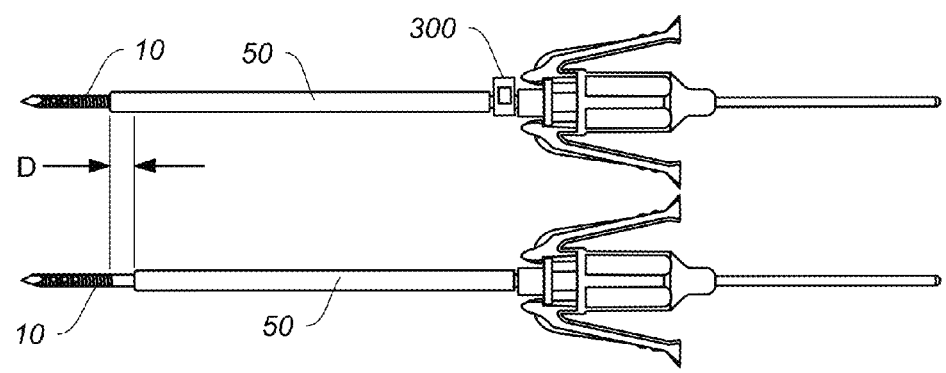
FIGS. 15B-15D show a method of using the spacer and delivery instrument of FIG. 14A.
Figure 15C:
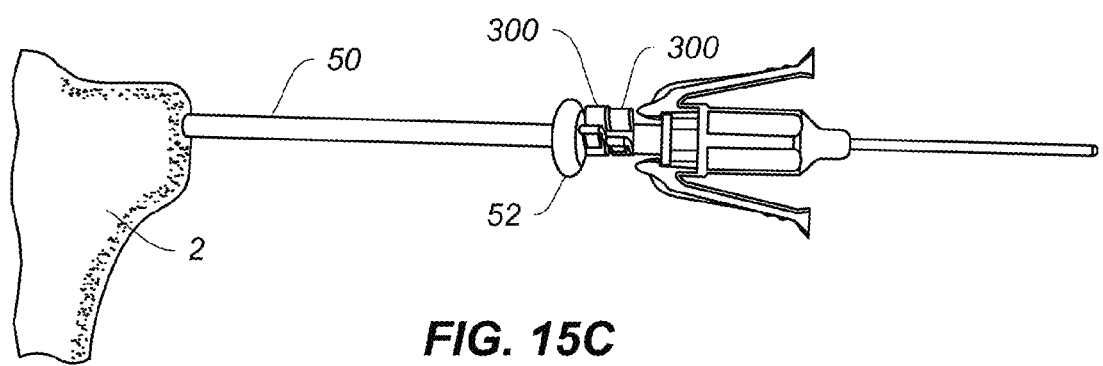

The spacer 300 may also be used with the sleeve 50 or other instrument with a tubing structure. The spacer 300 could be added or removed before or after the sleeve 50 is slid over the cannula 30 or pin 10. In some embodiments, the spacer 300 may represent an incremental width, such as for example, 5, 10 or 15 mm, without limitation. More than one spacer 300 may be used simultaneously to build the required depth stop, as shown in FIG. 15A and 15C.

Figure 15D:
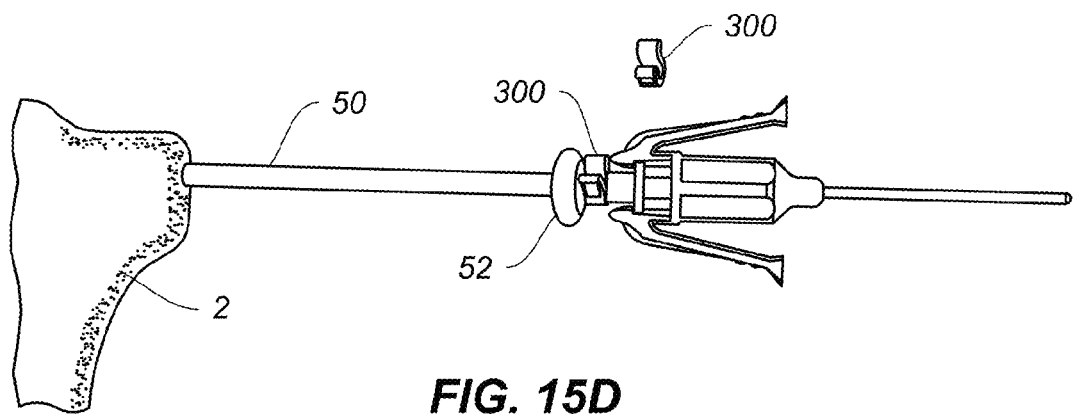

In use, the spacer 300 is configured to control the depth drilled into bone. The spacer 300 acts as a hard stop to prevent overdrilling. Additionally, the spacer 300 may be useful for confirming that a minimum cannula penetration has been achieved. For example, as shown in FIG. 15B, when the spacer 300 is removed, the pin 10 can be drilled the additional spacer 300 width D, and hence the depth corresponding to the spacer width D. As mentioned, more than one spacer 300 may be used or removed at any time. The spacer 300 may advantageously be removed without removing the sleeve 50 or other forms of depth control, as shown in FIG. 15D.

Figure 16:
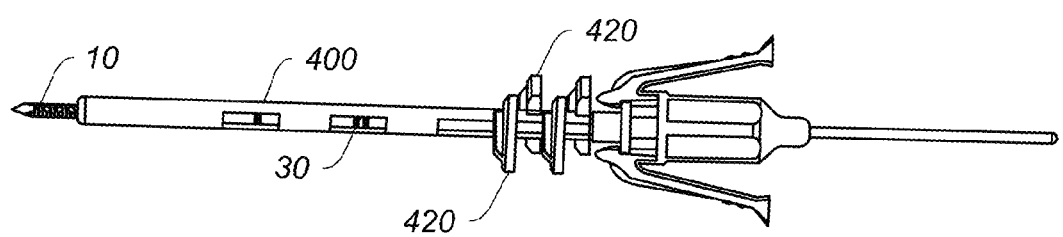
FIG. 16 shows an exemplary embodiment of a breakaway adjustable spacer body in use with a cannulated delivery pin of the present disclosure.
Figure 17:
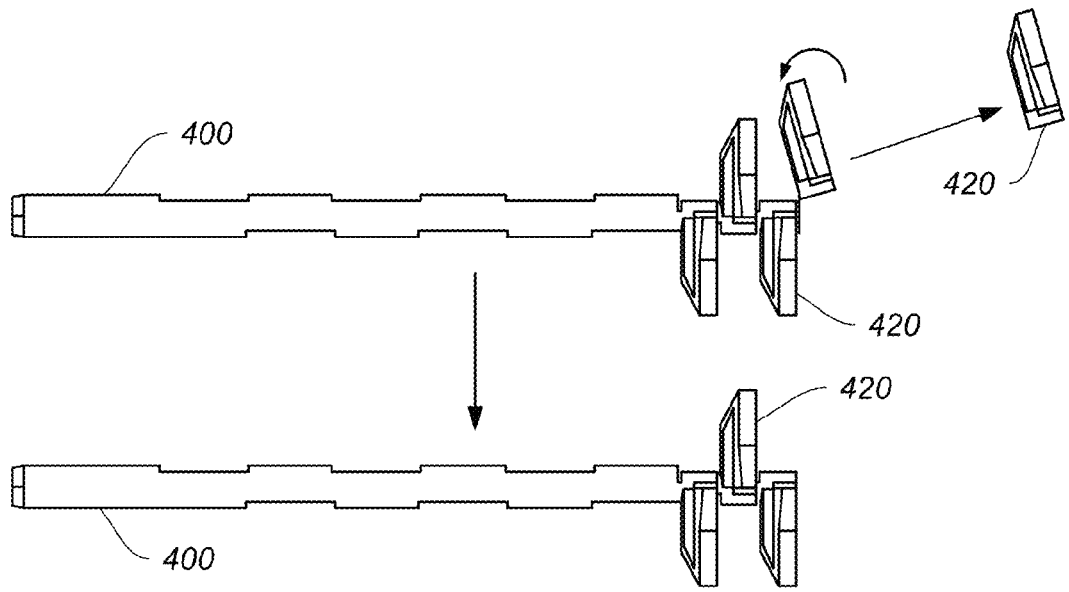
FIG. 17 shows a method of using the adjustable spacer body of FIG. 16.
Figure 18A:
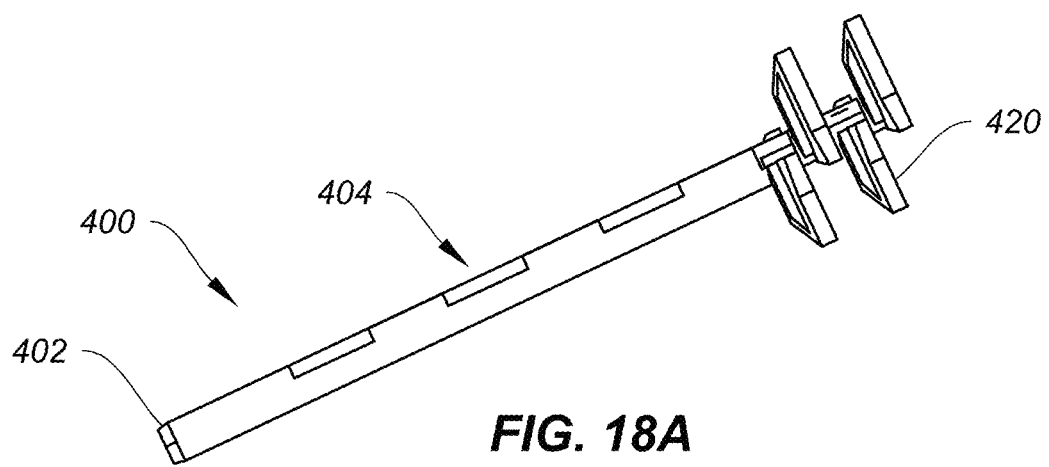
FIG. 18A shows another perspective view of the adjustable spacer body of FIG. 16.

FIGS. 16, 17, 18A and 18B show another exemplary embodiment of a depth control feature of the present disclosure. As shown in FIG. 16, the depth control feature may comprise an adjustable tubular body 400 having breakaway spacer segments 420 configured for placement over instruments such as pin 10 or cannula 30. Initially, the tubular body 400 and spacer segments 420 may be provided as an integral piece, such as for example injection molded plastic, and may further include coring or cutaway sections 404, as shown in FIG. 18A. After placement over a cannula 30 or pin 10, the spacer segments 420 may be incrementally removed to allow deeper drilling, as illustrated in FIG. 17. The spacer segments 420 may be configured to break off, or snap off, easily from the tubular body 400. The tubular body 400 may comprise a plurality of spacer segments 420. The width of the spacer segments 420 may vary and be determined at the manufacturing stage. The spacer segments 420 are configured to break off and be removed from the tubular body 400 without disturbing any other component, such as the cannula 30 or pin 10 within the tubular body 400.

Figure 18B:
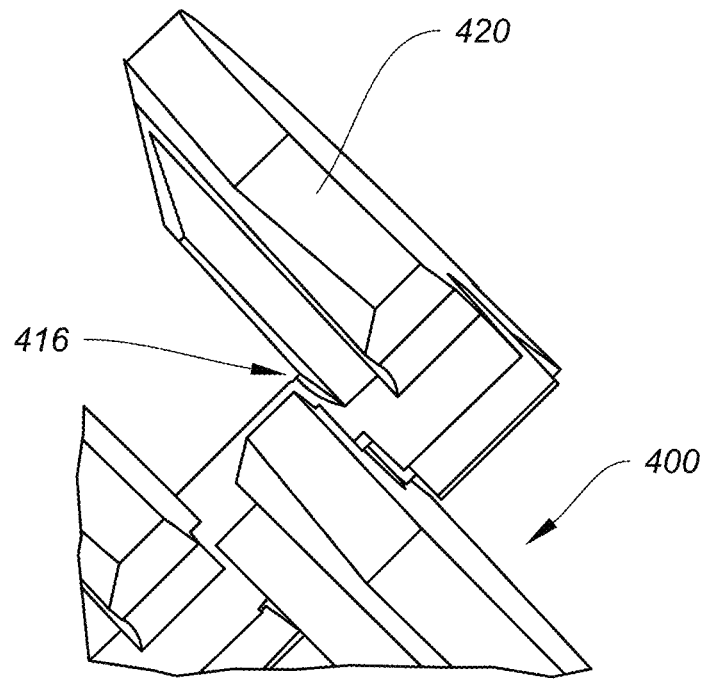
FIG. 18B shows an enlarged view of the adjustable spacer body of FIG. 18A.

FIG. 18B shows an enlarged view of the tubular body 400 and spacer segments 420. The tubular body 400 may be injection molded, as mentioned above, and have a tubular structure with a diameter sufficient to slide over the cannula 30 or pin of the present disclosure. Further, the tubular body 400 may be provided with an edge 402 that is configured to contact bone. To allow the spacer segments 420 to break off easily from the tubular body 400, the area 416 representing the intersection of the segments 420 to the tubular body 400 may be geometrically weaker, such as shown. For example, the break away location could have less real estate, be thinner or have scoring or perforations to weaken the area.

While the adjustable tubular body 400 shown in FIGS. 18A and 18B may be a single unitary body formed of the same material, it is contemplated that the adjustable tubular body may also comprise a combination of different materials. For example, an exemplary embodiment of an adjustable tubular body 400' is shown in FIGS. 19A and 19B. The tubular body 400' may be a composite of a metal tubular body with plastic breakaway spacer segments 420' attached thereto. Unlike tubular body 400, the main body of tubular body 400' may be solid metal with no windows or cutout portions. Similar to tubular body 400, the tubular body 400' of FIGS. 19A and 19B may be configured with a diameter sufficient to slide over the cannula 30 or pin of the present disclosure, and may be provided with an edge that is configured to contact bone 2, as shown in FIG. 19B.

Other embodiments will be apparent to those skilled in the art from consideration of the specification and practice of the embodiment disclosed herein. It is intended that the specification and examples be considered as exemplary only, with a true scope and spirit of the embodiment being indicated by the following claims.

What is claimed is:

1. A device to control a depth of insertion into a bone, comprising:
    a tool extending between a tip and a tool-engaging end; and
    an adjustable spacer body including:
        a tubular body for receiving the tool, the tubular body including a bone engaging end configured to rest against cortical bone; and
        a plurality of spacer clips attachable to a portion of the tubular body at a structurally weakened area to enable breakaway removal of one or more of the plurality of spacer clips.

2. The device of claim 1, wherein the tubular body includes one or more cutout sections.

3. The device of claim 1, wherein the plurality of spacer clips and the tubular body are formed from a composite of materials.

4. The device of claim 3, wherein at least one of the materials is metal.

5. The device of claim 1, wherein the tool is a pin comprising a cannulated shaft including one or more fenestrations.

6. The device of claim 5, wherein the tip of the pin includes at least one cutting edge.

7. A system for controlling a depth of insertion into a bone, comprising:
    a pin comprising a cannulated shaft extending between a tip and a tool-engaging end, the shaft including one or more fenestrations near the tip, the tip comprising one or more cutting edges;
    a guide including one or more drilling portals configured to receive the pin; and
    a depth control device configured to control a depth of insertion of the pin into a bone including the subchondral bone defect, the depth control device including:
        an adjustable spacer body including:
            a tubular body for receiving the pin; and
            a plurality of spacer clips attached to a portion of the tubular body at a structurally weakened area to enable breakaway removal of the plurality of spacer clips.

8. The system of claim 7, wherein the pin comprises visual markers to indicate depth.

9. The system of claim 7, wherein the pin comprises radiopaque markers to indicate depth.

10. The system of claim 7, wherein the pin comprises a sensory tip connected to a sensory line for receiving feedback from an area in contact with said tip.

11. The system of claim 7, wherein the guide includes one or more trajectory indicators.

* * * * *